(12) United States Patent
Masters et al.

(10) Patent No.: US 7,935,364 B2
(45) Date of Patent: May 3, 2011

(54) PATTERNED GRADIENT WOUND DRESSING AND METHODS OF USING SAME TO PROMOTE WOUND HEALING

(75) Inventors: Kristyn Simcha Masters, Madison, WI (US); Tracy Jane Stefonek, Cottage Grove, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 12/041,881

(22) Filed: Mar. 4, 2008

(65) Prior Publication Data
US 2009/0226506 A1 Sep. 10, 2009

(51) Int. Cl.
*A61F 13/00* (2006.01)
*A61F 15/00* (2006.01)
*A61L 15/16* (2006.01)

(52) U.S. Cl. .......................... 424/443; 424/447; 602/50

(58) Field of Classification Search ........................ None
See application file for complete search history.

(56) References Cited

U.S. PATENT DOCUMENTS

| | | | |
|---|---|---|---|
| 6,596,296 B1 * | 7/2003 | Nelson et al. | 424/426 |
| 2003/0175410 A1 * | 9/2003 | Campbell et al. | 427/2.24 |
| 2005/0026836 A1 * | 2/2005 | Dack et al. | 514/12 |

FOREIGN PATENT DOCUMENTS

WO   WO 2007/085626   *   8/2007

OTHER PUBLICATIONS

Chung et al., Biomaterials, 23(24):4803-4809, 2002.*
Mi et al., Biomaterials, 22:165-73, 2001.*
Karakecili et al., Acta Biomateriala, 4(4):989-96, 2008 (available on-line Feb. 19, 2008).*
Chen et al. Biomaterials, 22(18):2453-7, 2001.*
Ito, Biomaterials, 20:23333-42, 1999.*
Kapur, T.A., et al., "Immobilized concentration gradients of nerve growth factor guide neurite outgrowth", J. Biomed. Mater. Res. A., 2004, 68A: 235-243.
Gobin, A.S., et al., "Effects of epidermal growth factor on fibroblast migration through biomimetic hydrogels", Biotechnol. Prog., 2003, 19: 1787-1785.
DeLong, S.A., et al., "Covalently immobilized gradients of bFGF on hydrogel scaffolds for directed cell migration", Biomaterials, 2005, 26:3227-3234.
Burdick, J.A. et al., "Fabrication of gradient hydrogels using a microfluidics/photopolymerization process", Langmuir, 2004, 20: 5153-5156.
Zaari, N., et al., "Photopolymerization in microfluidic gradient generators: microscale control of substrate compliance to manipulate cell response", Adv. Mater., 2004, 16: 2133-2137.
Masters, K.S., et al. "Immobilized gradients of epidermal growth factor promotes accelerated and directed keratinocyte migration", Wound Repair Regen., 2007, 15 (6): 847-855.
Stefonek-Puccinelli, T.J., et al. "Co-immobilization of gradient-patterned growth factors for directed cell migration", Ann. Biomed. Eng., 2008, 36 (12): 2121-2133.

* cited by examiner

*Primary Examiner* — Marianne P Allen
(74) *Attorney, Agent, or Firm* — Quarles & Brady LLP

(57) ABSTRACT

The present invention provides a wound dressing that includes a patterned gradient of immobilized growth factor molecules that promote directed migration of cells during dermal wound healing. Growth factor is immobilized on a support substrate to present a gradient pattern of increasing growth factor concentration to migrating cells. Methods of promoting wound healing using the patterned gradient wound dressing and fabrication methods of same are also provided.

20 Claims, 18 Drawing Sheets

(a) NSDSECPLSHDGYCLHDGVCMYIEALDKYACNCVVGYIGERCQYRDLKNWELR (a)

| Distance up gradient (mm) | ng/cm² EGF |
|---|---|
| 0.25 | 0.354 |
| 3 | 1.746 |
| 6 | 3.156 |
| 9 | 4.408 |
| 12 | 5.410 |
| 13.5 | 5.880 |
| 15 | 6.189 |
| 18 | 6.638 |

(b)

| Distance up gradient (mm) | ng/cm² EGF |
|---|---|
| 0.25 | 0 |
| 3 | 0.409 |
| 6 | 1.496 |
| 9 | 2.516 |
| 12 | 4.813 |
| 13.5 | 5.816 |
| 15 | 6.939 |
| 18 | 9.290 |

(c)

(d)

SEQUENCE LISTING

<160> NUMBER OF SEQ ID NOS: 1

<210> SEQ ID NO 1
<211> LENGTH: 53
<212> TYPE: PRT
<213> ORGANISM: Homo sapiens

<400> SEQUENCE: 1

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Asn Trp Glu Leu Arg
    50

PATTERNED GRADIENT WOUND DRESSING AND METHODS OF USING SAME TO PROMOTE WOUND HEALING

STATEMENT REGARDING FEDERALLY SPONSORED RESEARCH

This invention was made with government support under Grant no. EB005440 awarded by the National Institutes of Health. The government has certain rights in the invention.

CROSS-REFERENCE TO RELATED APPLICATIONS

Not applicable.

FIELD OF THE INVENTION

The present invention relates to the field of wound healing. More particularly, the present invention relates to patterned gradient wound dressings and their use in the promotion of wound healing.

BACKGROUND OF THE INVENTION

Approximately 5-7 million Americans are afflicted with chronic skin wounds that account for billions of dollars in medical expenses each year.[1,2] The incidence of chronic wounds is expected to increase dramatically[3] due to an increased elderly population and incidence of diabetes, a disease that is accompanied by wound-healing deficiencies.[4] In the United States, at least 82,000 lower-limb amputations are performed annually due to diabetic ulcers.[5]

Cell migration is an essential event in wound repair throughout the body. In tissues ranging from skin to blood vessels to bone, the migration of cells is critical for healing and regeneration.[6-8] In dermal tissue repair, the migration of keratinocytes from the wound edges helps to close the wound, with re-epithelialization viewed as a hallmark of successful wound care. Early re-epithelialization initiates wound remodeling within the underlying granulation tissue, and early wound closure reduces the chance of developing hypertrophic scarring or other related problems.[9] Growth factors and other mitogens often provide the molecular cues that induce cell migration.[10] Growth factor deficiencies lead to impaired wound healing, as reduced levels of numerous growth factors have been observed in chronic wounds when compared with normal acute wounds.[11-13]

One of the most important factors in epidermal cell growth and migration is epidermal growth factor (EGF).[6,14] EGF is released in abundance by platelets at the wound site and is one of several growth factors that are deficient in chronic wounds. This growth factor has been credited with playing a prominent role in wound closure through stimulation of epithelial cell migration and proliferation; EGF also reduces scarring by preventing excessive wound contraction.[15] Accordingly, cell migration directed by one or more growth factors is a critical element in wound healing, and it is believed that the ability to control the migration direction of cells will lead to accelerated closure of wounds.

Commonly used approaches to treat chronic or acute wounds are typically based on simple wound care regimens involving debridement, cleaning, and application of moist dressings.[16] More advanced dressings such as growth factor-containing topical gels[17,18] have met with only limited clinical success, largely due to the inadequate delivery and persistence of the growth factor at the wound site.[19] Many growth factors, including EGF, require prolonged exposure to cells in order to elicit a response,[20] explaining why a single topical growth factor application often fails. Topically applied agents, such as growth factors, are rapidly washed off the wound by exudation or absorbed into the wound dressing. In fact, the available amount of topically applied basic fibroblast growth factor in solution decreases by 50% within 4 hours of contact with sterile gauze,[21] and reapplication of growth factors is often cost prohibitive. Furthermore, growth factors in the physiological environment can be rapidly degraded or otherwise rendered inactive before reaching their target.

Covalent tethering of growth factors to biomaterials has the potential to ameliorate many of these problems, and possibly result in increased availability of active growth migration signals, coupled with precise control over cell migration direction. Patterning polymeric surfaces with bioactive molecules is becoming an attractive method for gaining specific control over cell adhesion and exploring cell function.[22-26] While the majority of patterning research has involved the creation of cell adhesion templates via patterning of peptide sequences or matrix proteins,[22-24] it is also possible to pattern-immobilize growth factors in the same manner.[25,27] Previous studies have shown that EGF retains its biological activity following chemical modification with photoactive molecules and surface immobilization via exposure to long-wavelength ultraviolet (UV) light.[28] In fact, immobilized EGF has proven to be more mitogenic for Chinese hamster ovary cells than free EGF.[28] This result is hypothesized to be due to the inability of cells to internalize immobilized EGF, a process that would normally lead to consumption of the growth factor and down-regulation of its receptors.

Acceleration of wound closure not only results in decreased patient suffering and cost of wound treatment but may also minimize scarring and lead to formation of a more stable closed wound.[9,34] A recent review of the use of growth factors in wound dressings concluded that the clinical outcomes of these materials have been "generally disappointing."[17] It is widely accepted that these lackluster results have been directly attributable to the manner in which growth factors were incorporated into the dressings, namely that the delivery methods did not allow for sustained growth factor availability or bioactivity. Thus, materials that deliver bioactive molecules in a manner that prolongs their availability and bioactivity would possess a significant advantage over existing dressings.

Moreover, providing a means to actively guide the direction or speed of cell migration would also have significant consequences for improvement of wound-healing therapies. Another major obstacle in implementing growth factor-based therapies has been the expense of the biomolecules, meaning that a system that improves healing responses using a reduced amount of growth factor could make growth factor based wound healing therapies more widely available. Therefore, there is a long felt need in the medical community for improved materials and methods that overcome one or more of the above-described obstacles in treating chronic wounds.

SUMMARY OF THE INVENTION

The present invention is based on the inventors' success in preparing platforms that are modified with gradients of immobilized growth factor, termed "patterned gradient wound dressings", that promote directed cell migration during dermal wound healing. Patterning techniques described herein enable precise control over the spatial location of immobilized growth factor and allow for ease of both wound dressing fabrication and quantitative characterization of gradient patterns of different types and slopes.

Accordingly, a first aspect of the present invention is directed to a patterned gradient wound dressing for promoting directed cell migration during dermal wound healing. Such a wound dressing includes: (a) a support substrate for placement on a dermal wound; and (b) a growth factor gradient immobilized to the support substrate. The growth factor gradient is characterized by an increasing concentration of growth factor that promotes directed cell migration across the growth factor gradient from low to high growth factor concentration during dermal wound healing. A preferred patterned gradient wound dressing includes a growth factor gradient having a exponentially increasing concentration of growth factor.

A wide variety of growth factors may be immobilized into/onto the support substrate of the wound dressing, including, but not limited to, epidermal growth factor ("EGF"), insulin-like growth factor 1 ("IGF-1"), basic fibroblast growth factor ("bFGF"), platelet-derived growth factor ("PDGF"), vascular endothelial growth factor ("VEGF"), keratinocyte growth factor ("KGF"), transforming growth factor alpha ("TGF-a"), transforming growth factor beta ("TGF-b") and mixtures thereof.

In certain embodiments, the support substrate will further include an extracellular matrix protein, such as collagen, fibronectin, or laminin, and, optionally, one or more angiogenesis factors including, but not limited to, matrix metalloproteinase ("MMP"), angiopoietins Ang1 or Ang2, or Delta-like ligand 4 ("Dll4").

The support substrate of the wound dressing may be made of a polymeric material. Useful polymeric materials for this purpose include, but are not limited to, polytetrafluoroethylene, polydimethylsiloxane, poly-vinylidine fluoride, polyethylene, polystyrene, polycarbonate, polyhydroxyethyl methacrylate, polyvinyl alcohol, polyvinyl chloride, polycaproamide, polyetheyleneoxide, polyethyleneterephthalate, polyacrylonitrile, silicones, polysilanes, polysiloxanes, polyurethanes, polylactides, polyglycolic acid, poly-beta hydroxybutyrate, polyepisilon caprolactone, polyanhyhdrides, polyorthoesters, polyiminocarbonates, mixtures thereof and copolymers thereof. In certain embodiments, the support substrate is made of an interpenetrating polymer network ("IPN") of at least two polymeric materials.

In yet other embodiments, the support substrate of the wound dressing is made of a sol-gel, a hydrogel, or a natural product. Suitable natural products for this purpose include, for example, alginates, gelatins, collagen, cellulose, fibrin, hyaluronan, polycarbohydates, mycoses, polyxyloses, chitans, polymers of amino glucoses, tragacanths, and latexes.

In a preferred embodiment, a wound dressing is provided that includes the growth factor EGF and the low to high growth factor concentrations across the growth factor gradient range from 0 ng/cm² to about 36 ng/cm², more preferably, from 0 ng/cm² to about 9 ng/cm².

Patterned gradient wound dressings according to the invention are characterized by a growth factor concentration across the growth factor gradient defined by a mathematical formula such as a power ($y=ax^b$), log ($y=a \ln(x)+b$) or linear ($y=mx+b$) equation. Particularly preferred patterned gradient wound dressings are characterized by a growth factor concentration across the growth factor gradient defined by a power ($y=ax^b$) formula.

In preferred embodiments, the wound dressings include a growth factor gradient that is spatially-oriented relative to the support substrate such that the low concentration of growth factor gradient is located along a periphery of the support substrate. Such orientation provides that the low concentration of the growth factor gradient is immediately adjacent to the dermal wound when the wound dressing is placed at the wound. The growth factor gradient of certain preferred embodiments is provided in the form of a radial pattern, as either a two dimensional radial patterned gradient or a three dimensional radial patterned gradient. The gradient may radiate from a central point of the dressing or may, alternatively, radiate from a point pre-selected during fabrication of the dressing.

Growth factors may be immobilized to the support substrate of the wound dressing by various methodologies known in the art, including but not limited to covalent linkage or high affinity interaction. Covalent linkages fabricated by the photo-patterning techniques described herein are the preferred mode of immobilizing growth factors to support substrate. Such techniques provide immobilization of growth factor to support substrate through covalent linkage formed by photoactivatable crosslinkers.

Immobilization of growth factor to support substrate may alternatively be accomplished by noncovalent interactions including, but not limited to, hydrophobic interactions, ionic interactions or high affinity interactions.

The present invention further contemplates a method for treating a dermal wound using the patterned gradient wound dressings described and claimed herein during the course of wound management. Dermal wounds to be treated by the present methods include acute dermal wounds, such as burns, as well as chronic wounds, such as diabetic ulcers and bed sores.

Yet another aspect of the invention provides a method of screening for agents that promote directed cell migration. Such a method includes steps of: (a) providing a support substrate and a test agent gradient immobilized to the support substrate; and (b) evaluating the ability of cells to migrate across the test agent gradient compared to a control that is treated with the same conditions but without the test agent gradient. An improvement in migration of cells across the test agent gradient relative to control indicates that the test agent promotes directed cell migration. The test agent gradient is preferably characterized by an exponentially increasing concentration of test agent across the test agent gradient from low to high test agent concentrations whereby the cells are evaluated for their ability to migrate from low to high test agent concentrations.

As can be appreciated, it is one object of the present invention to provide a patterned gradient wound dressing which provides improved promotion of wound healing. This invention provides the advantage over prior technologies in that embodiments of the invention utilize or are based on an exponentially increasing growth factor gradient, as recently characterized by the present inventors and described herein. Other objects, features and advantages of the present invention will become apparent after review of the specification, claims and drawings.

Solid line: 0 minute, UV exposure; horizontal dashes: 1 minute; vertical dashes: 2 minutes; open circles: 5 minutes.

Figure 3:
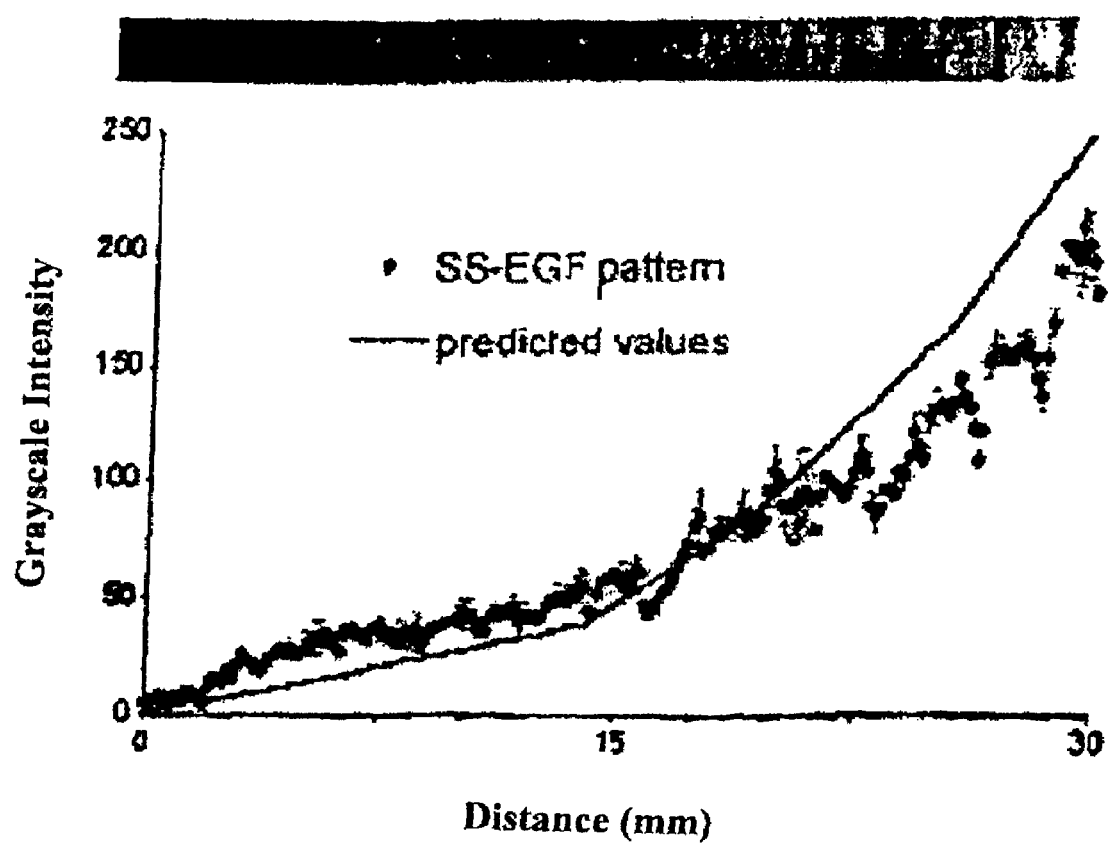

FIG. 3. Top, photomicrograph of fluorescently labeled SS-EGF patterned on a polystyrene surface (20× magnification), and bottom, corresponding graph of the increasing concentration gradient of immobilized EGF. Predicted intensities are based upon the original photomask pattern.

Figure 4:
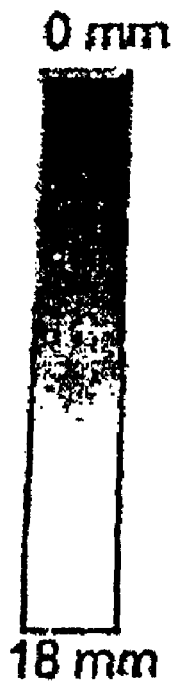
Figure 4:
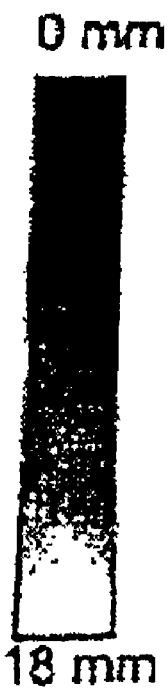
Figure 4:
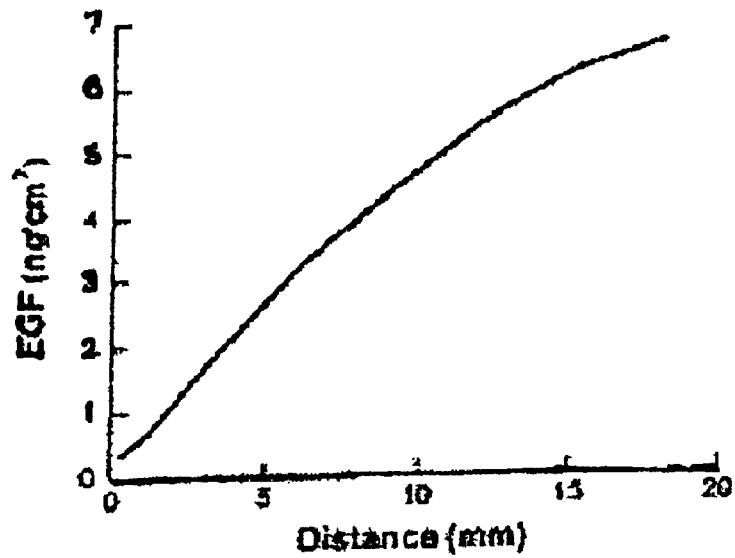
Figure 4:
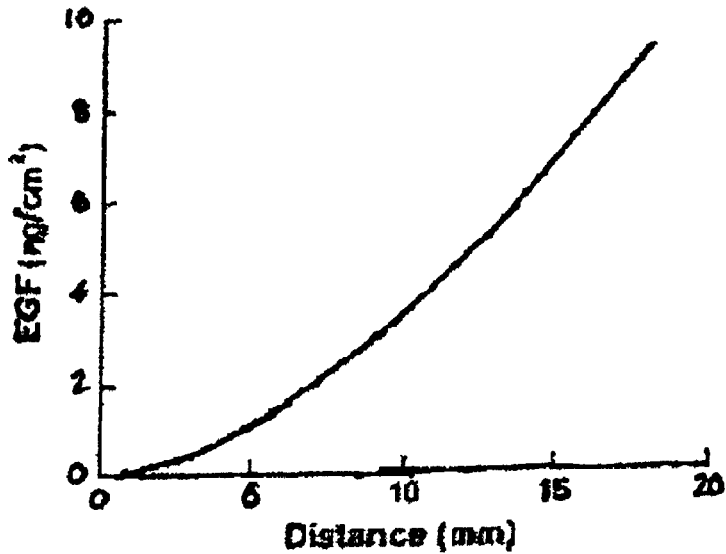

FIG. 4. Adobe Illustrator images used to create photomask films, the mathematical descriptions of the pictured gradients, and calculated EGF concentrations ng/cm$^2$) at several points along the gradients for both (A) 65% and (B) 35% gradients.

Figure 5:
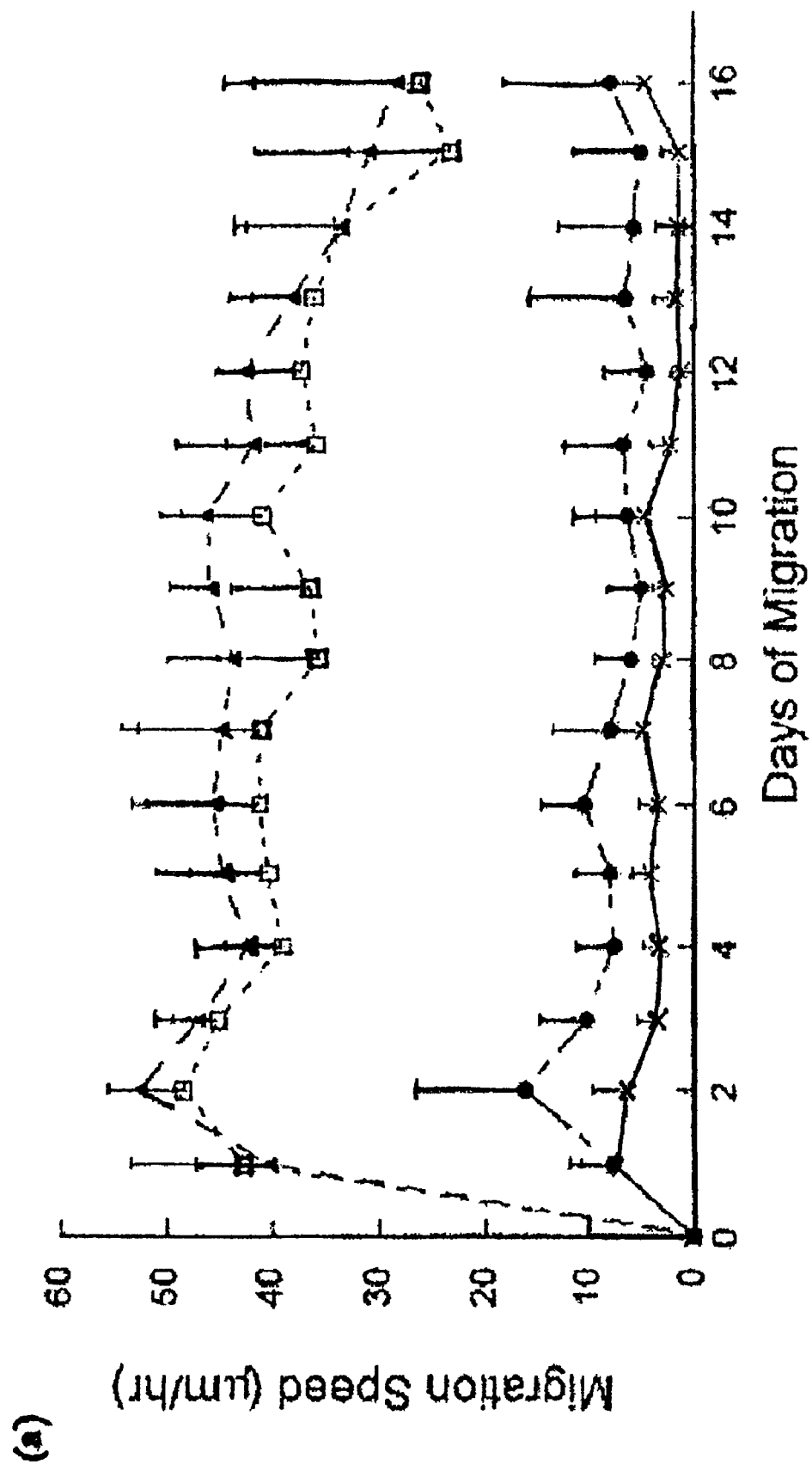
Figure 5:
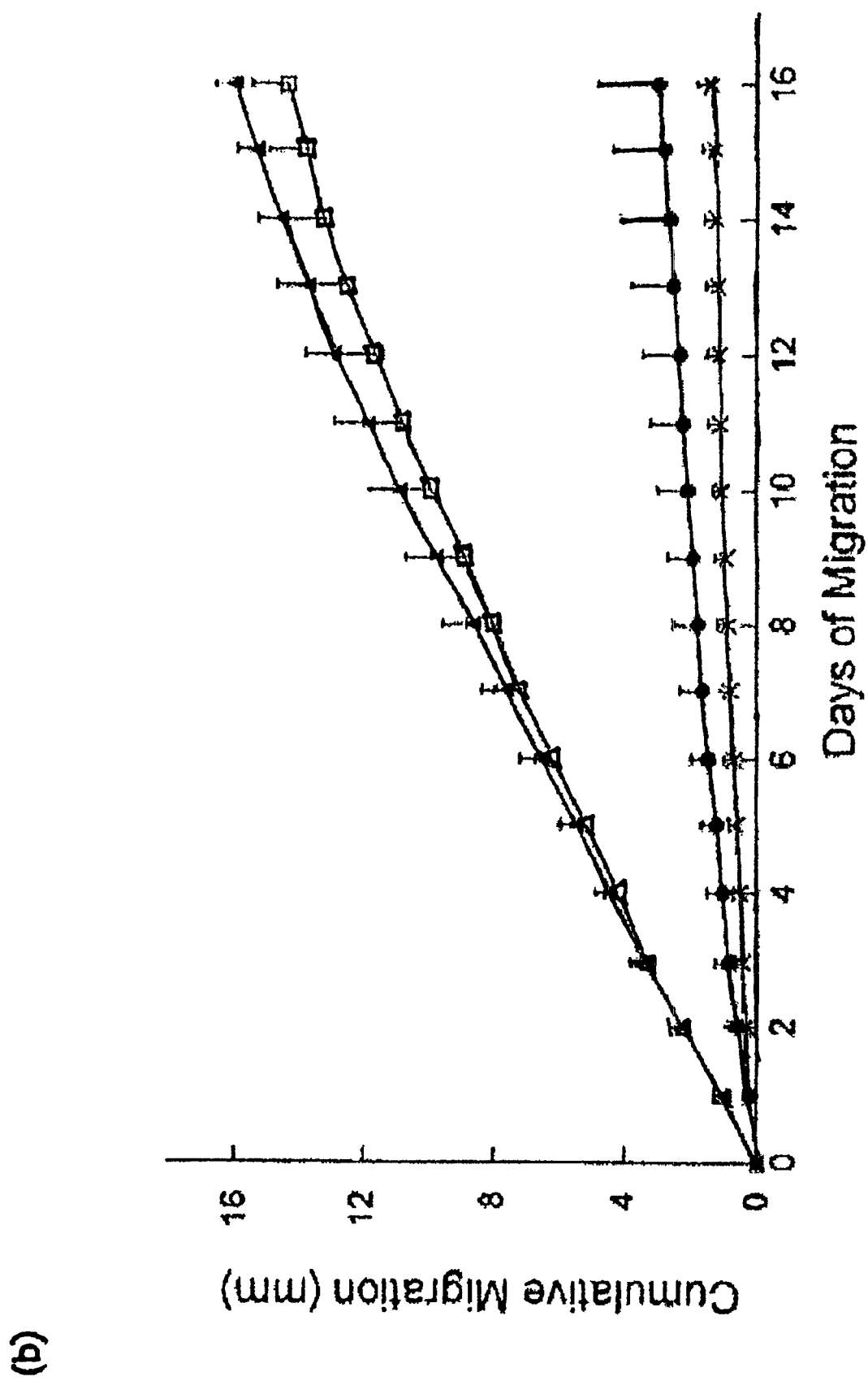

FIG. 5. (A) Average daily migration speed (μm/hour) of HaCaTs on TCPS, SS, 35%, and 65% SS-EGF gradients. (B) Average cumulative unidirectional migration distance (mm) of HaCaTs on TCPS, SS, 35%, and 65% SS-EGF gradients. Legend: ▲, 35% SS-EGF gradient; ⊔,65% SS-EGF gradient; ●, SS only; x-TCPS. N=5-7 per condition, p<0.001 for all SS-EGF samples at every time point after Day 0 when compared against either TCPS or SS controls. TCPS, tissue culture polystyrene.

Figure 6:
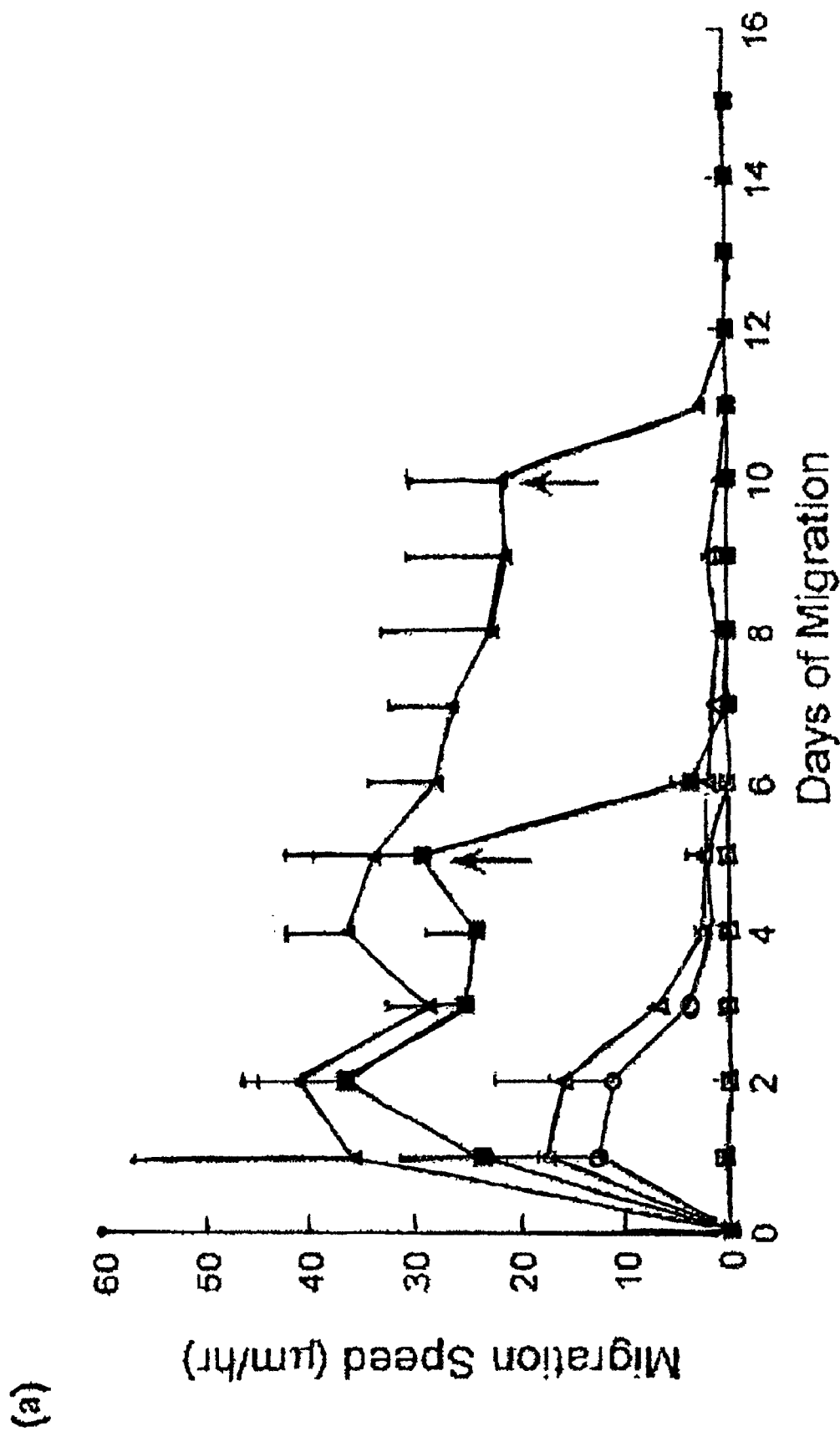
Figure 6:
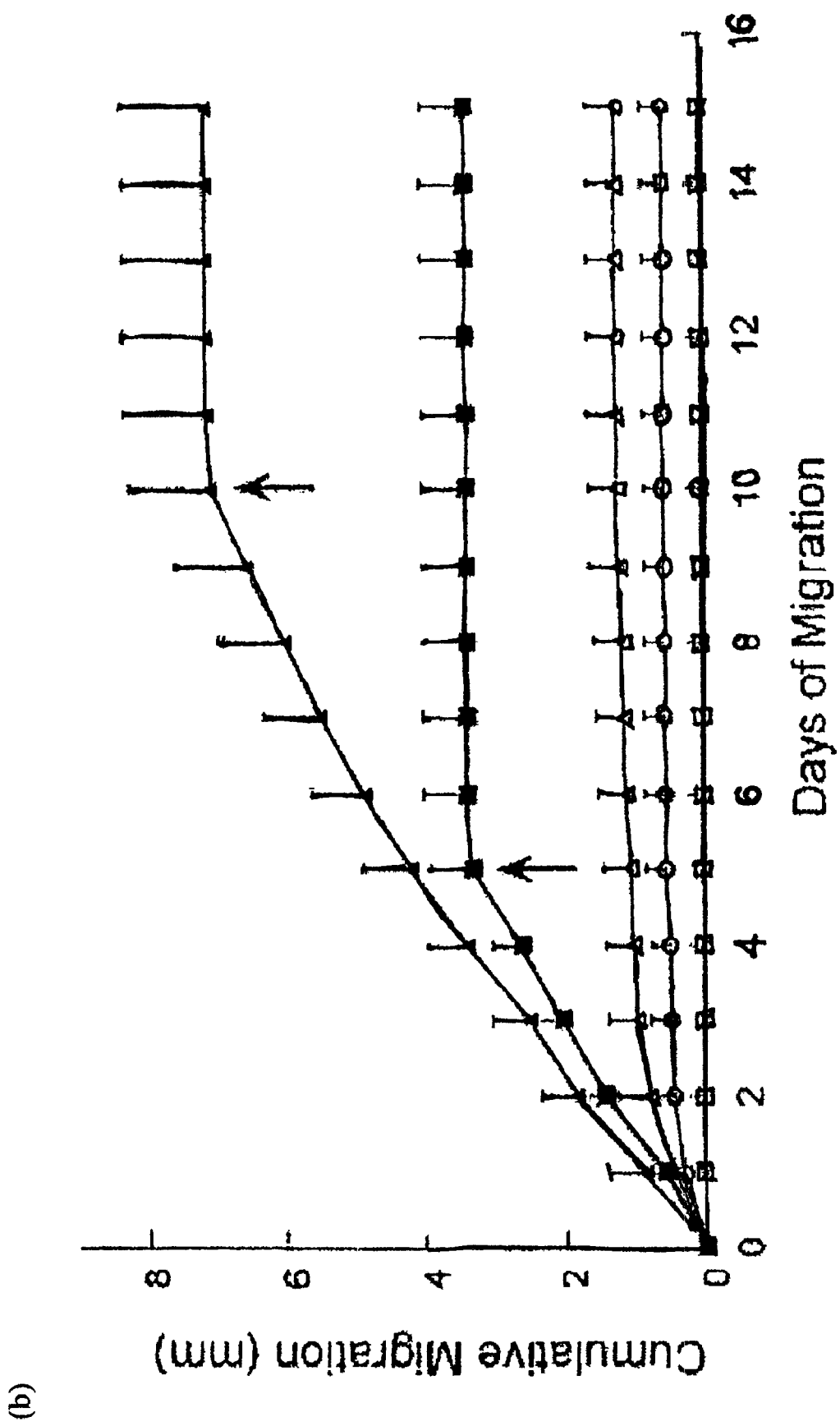

FIG. 6. (A) Average daily migration speed (μm/hour) of HaCaTs on TCPS and 35% SS-EGF gradient. Arrows indicate addition of PD168393 to one set of samples on Day 5 and a separate sample set on Day 10. (B) Average cumulative unidirectional migration distance (mm) of HaCaTs on TCPS, and 35% SS-EGF gradients. Legend: PD168393 added on Day 0 to SS-EGF (x) and TCPS (□), on Day 5 to SS-EGF (■) and TCPS (○), and on Day 10 to SS-EGF (▲) and TCPS (Δ). N=34 per condition, p<0.001 for all SS-EGF samples at every time point between Day 2 and the addition of PD168393 when compared against either TCPS or SS controls.

Figure 7:
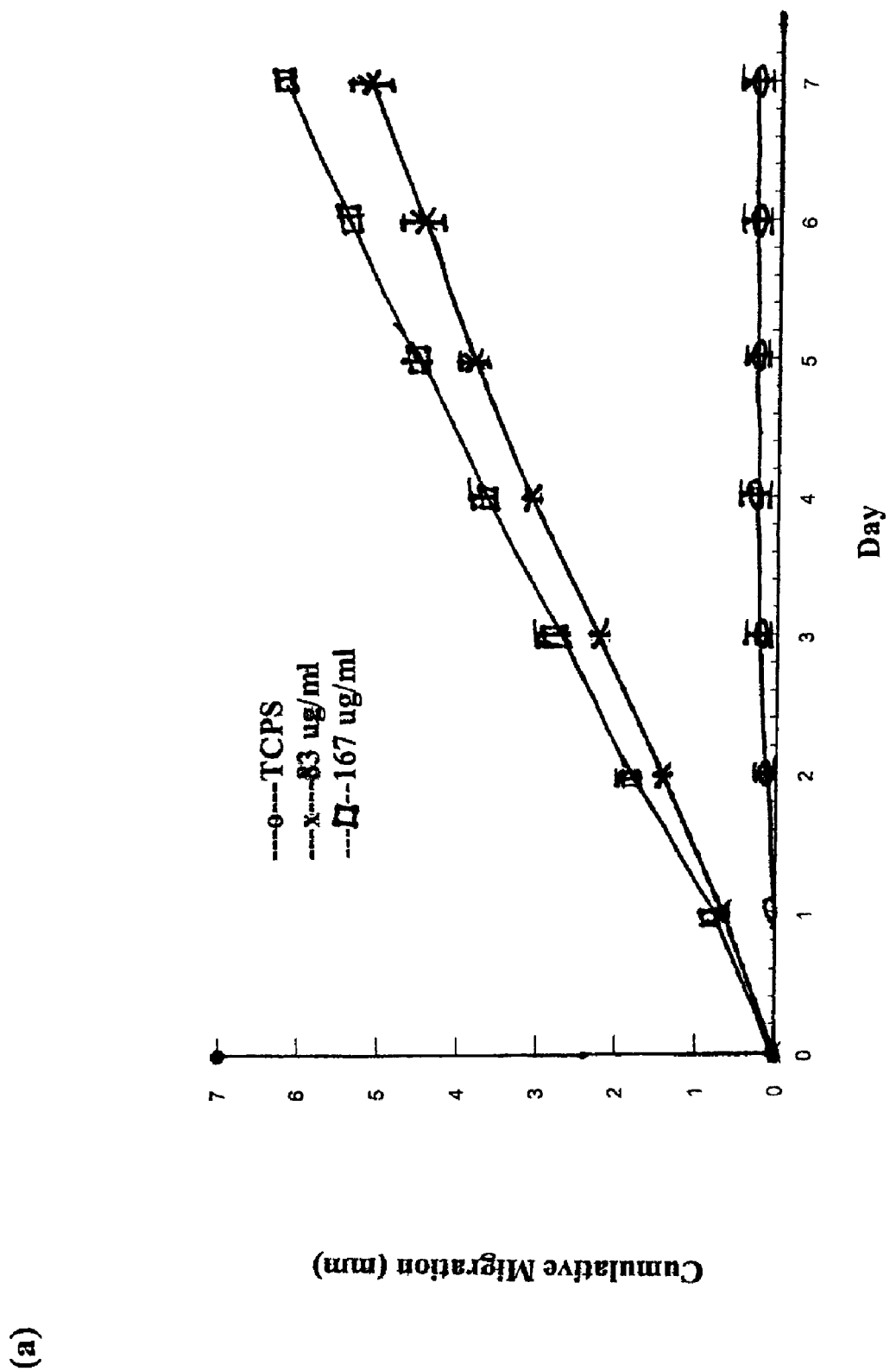
Figure 7:
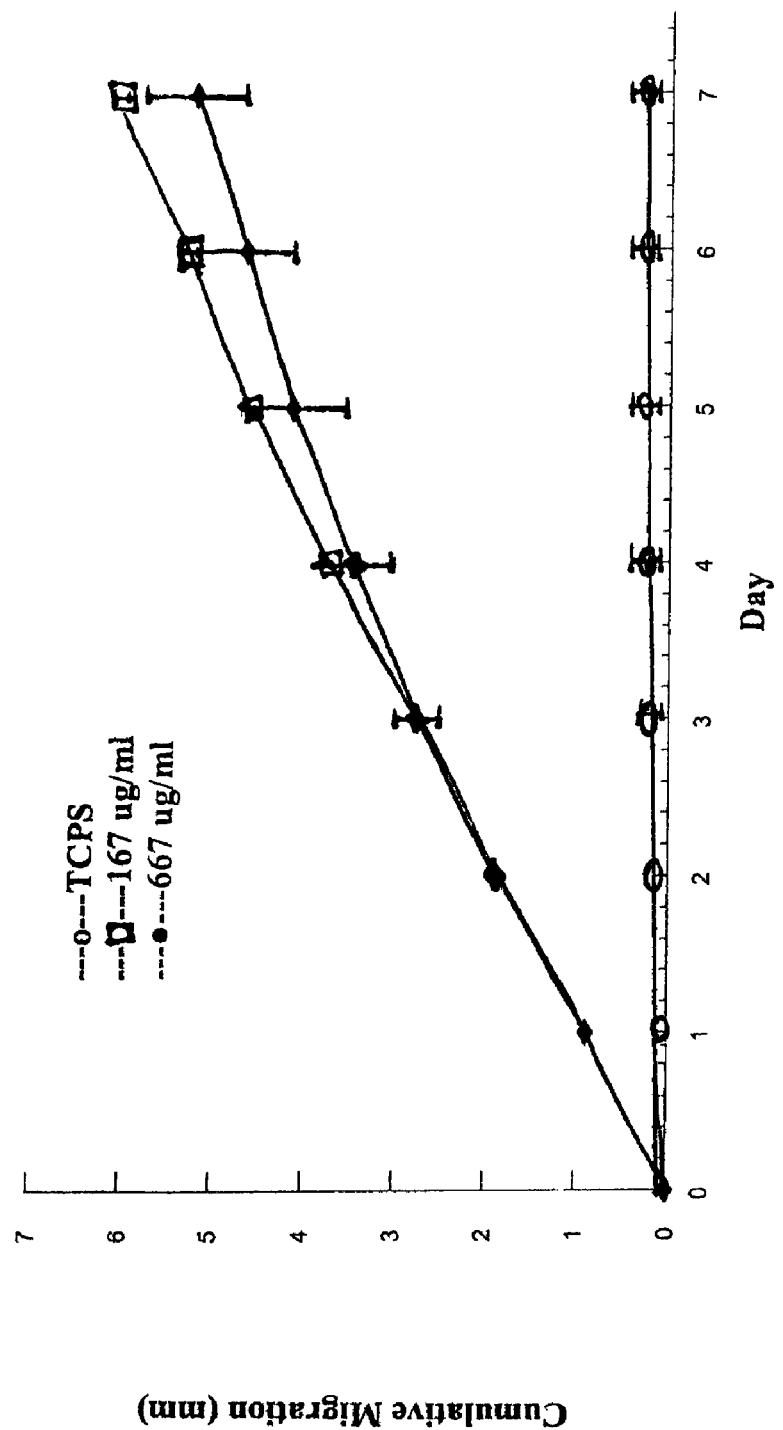
Figure 7:
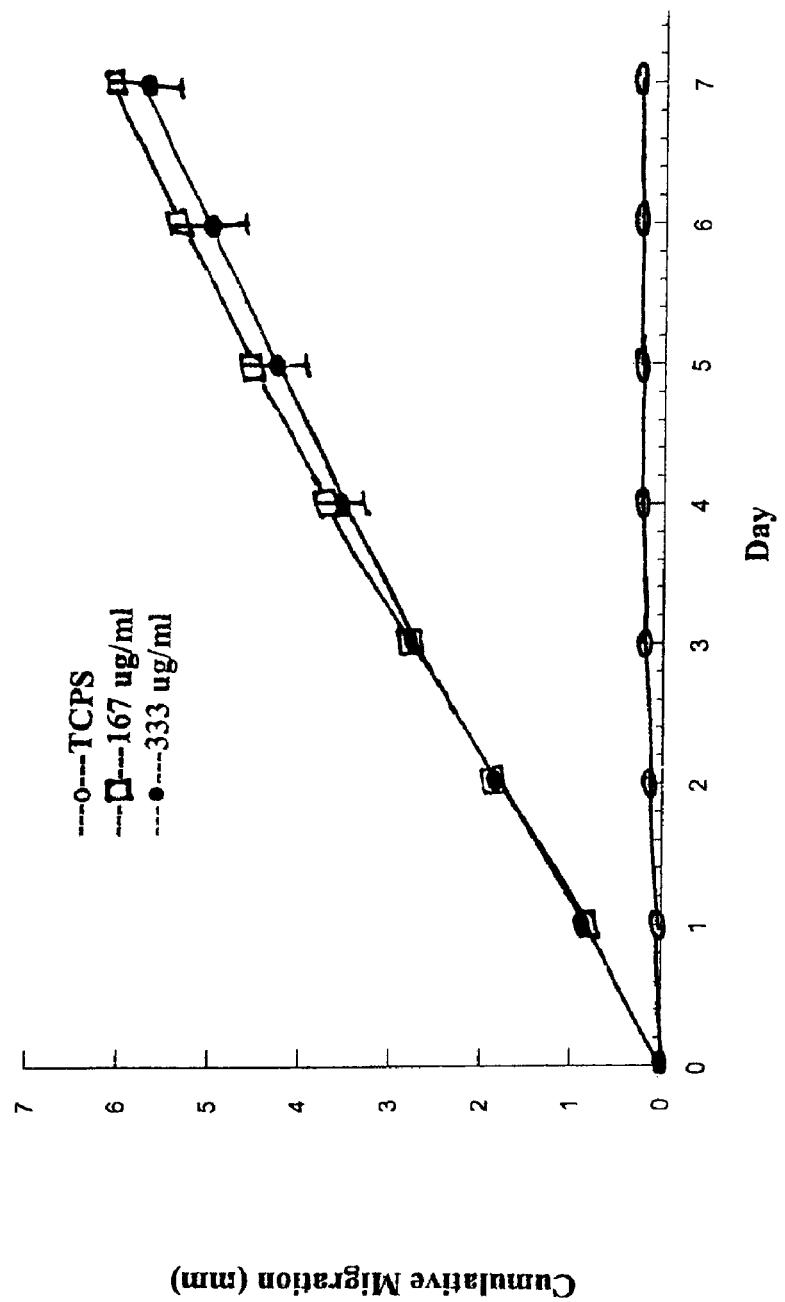
Figure 7:
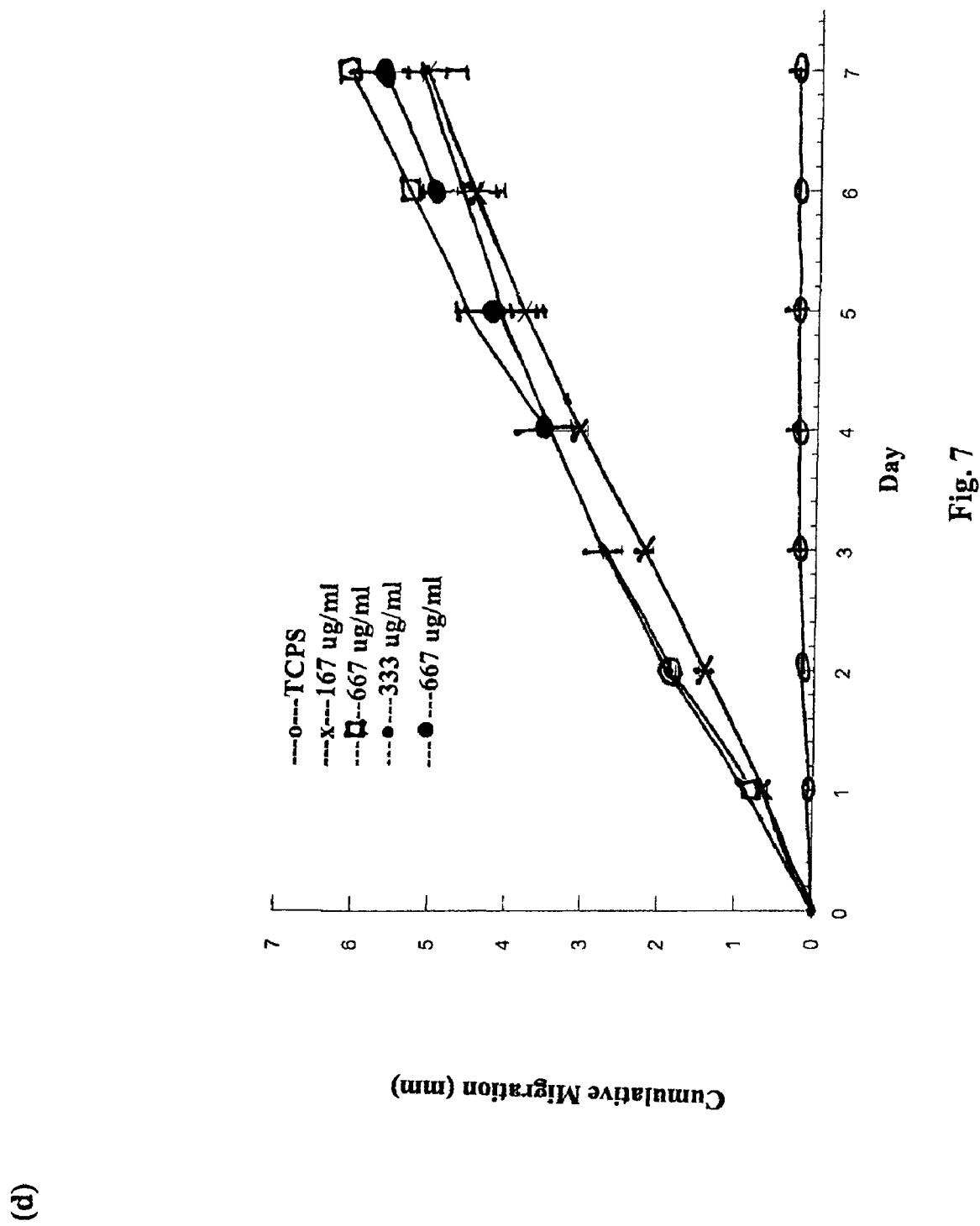

FIG. 7. Graphs showing effects of varying concentration of EGF during gradient pattern preparation and its effect on directed keratinocyte migration.

Figure 8:
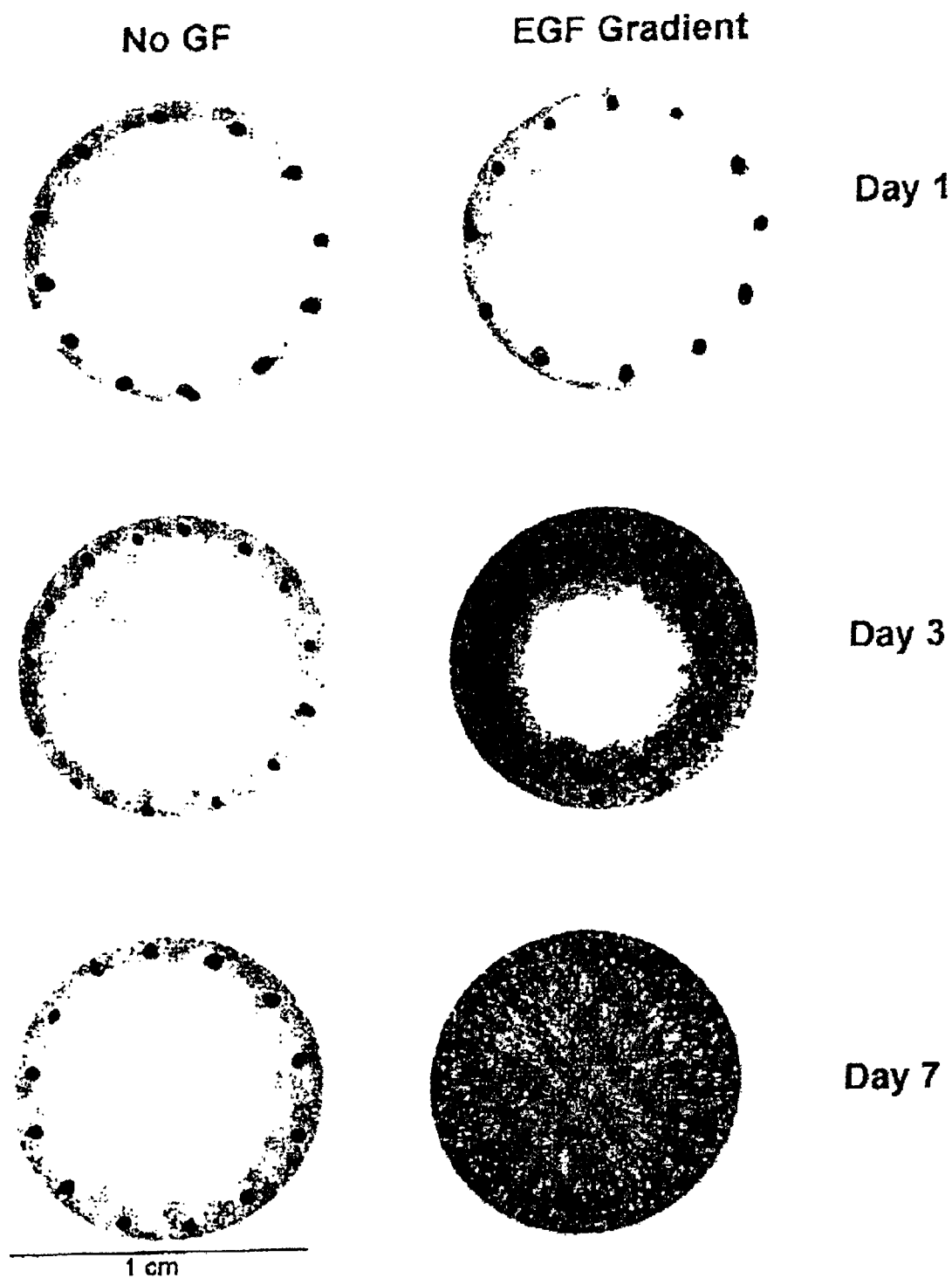

FIG. 8. Hematoxylin-stained HaCaTs at days 1, 3 and 7.3.5×, n=3 (left column) TCPS control; (right column) SS-EGF radial gradient.

Figure 9:
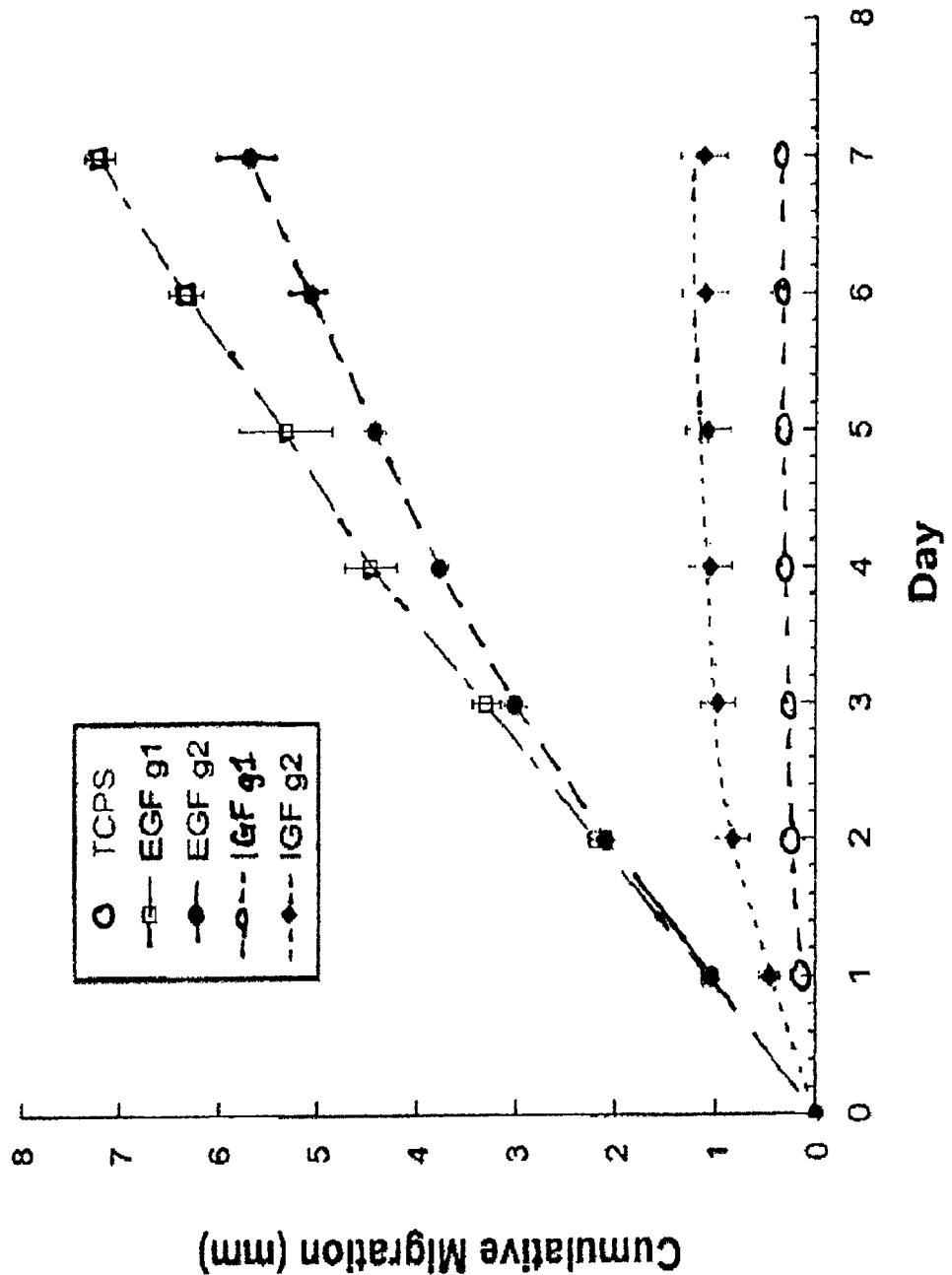
Figure 9:
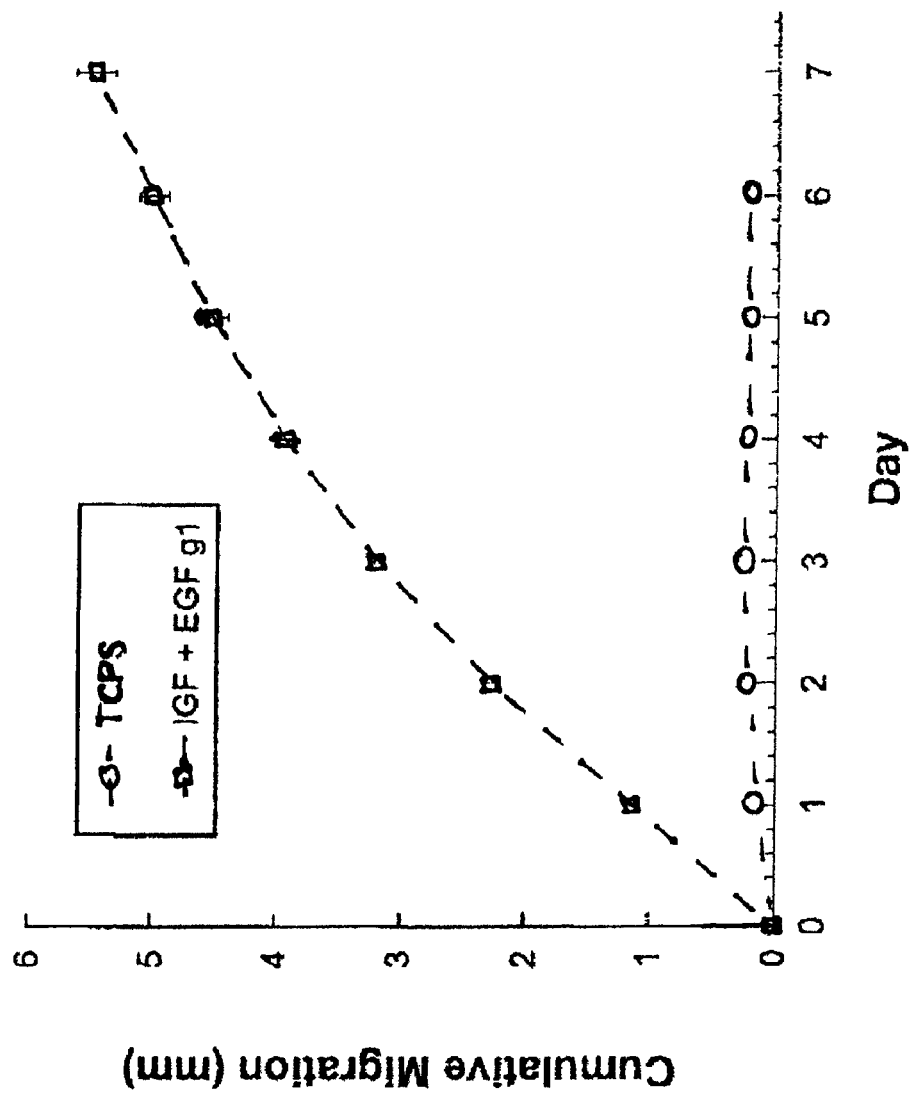

FIG. 9. (upper panel) Average cumulative migration of HaCaTs in mm on TCPS, EGF [g1], EGF [g2] IGF-1 [g1] and IGF-1 [g2]. (lower panel) Average cumulative migration of HaCaTs in mm on TCPS and IGF plus EGF [g1].

Figure 10:
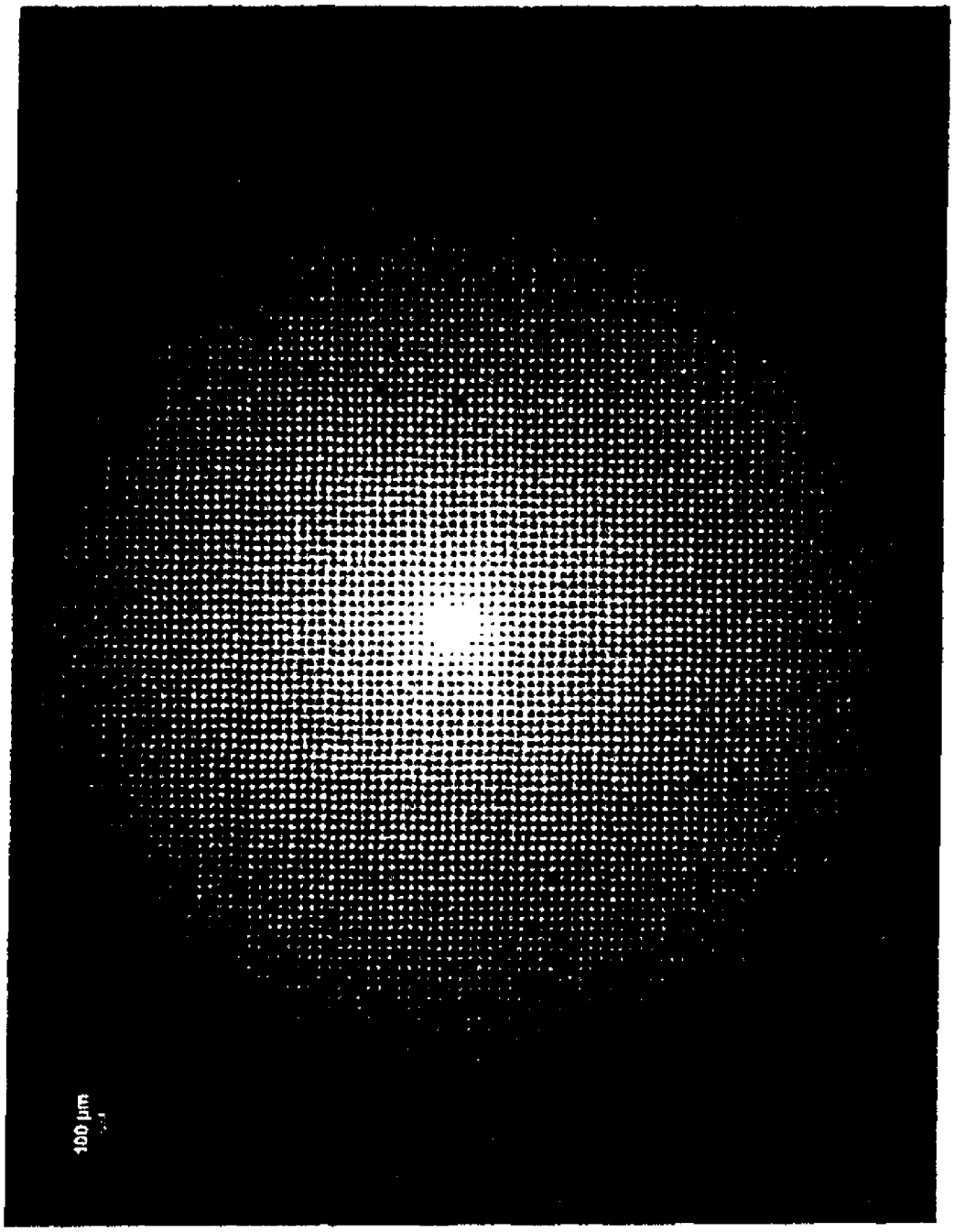

FIG. 10. Micrograph of 20% gradient ([g1]) photomask film.

Figure 11:
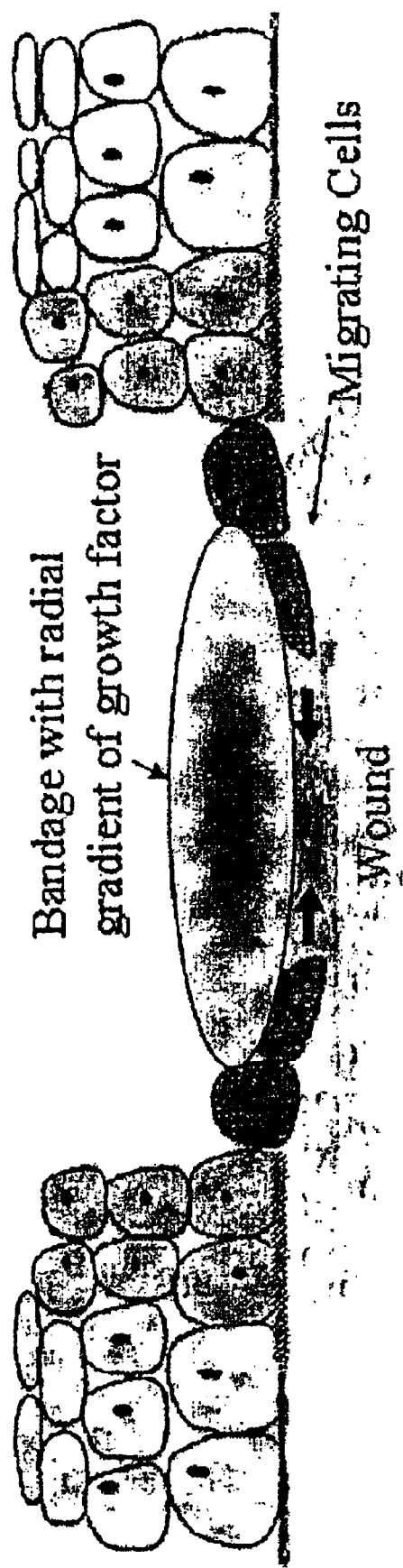

FIG. 11. Illustration of a patterned gradient wound dressing placed at a wound site.

DETAILED DESCRIPTION OF THE INVENTION

I. In General

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the materials, chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Immunochemical Methods In Cell And Molecular Biology (Mayer and Walker, eds., Academic Press, London, 1987); and Handbook Of Experimental Immunology, Volumes I-IV (D. M. Weir and C. C. Blackwell, eds., 1986).

The nucleotides and amino acids which occur in the various sequences appearing herein have their usual single-letter designations used routinely in the art. In the present specification and claims, references to Greek letters may either be written as alpha, beta, etc. or the corresponding Greek letter symbols (e.g., α, β, etc.).

II. The Invention

The present inventors have described and demonstrated the utility of an exemplary model system that provides support substrates modified with growth factor gradients which promote directed cell migration. The inventors utilization of photo-patterning techniques enabled precise control over the spatial location of immobilized growth factor and, as well, ease of fabrication and quantitative characterization of gradient patterns of different types and slopes. Under serum-free conditions in an exemplary system, the inventors demonstrated that human epidermal keratinocytes on immobilized EGF gradients preferentially migrated in the direction of higher EGF concentrations, and exhibited unidirectional migration speed and distance that was five- to twenty-fold (depending upon gradient pattern) greater than that observed on control surfaces. Treatment of migrating cells with an inhibitor of the growth factor receptor resulted in immediate cessation of migration, thus verifying that the observed migration trends were directly attributable to cell interactions with the immobilized growth factor.

Accordingly, a first aspect of the present invention is directed to patterned gradient wound dressings for promoting directed cell migration during dermal wound healing. Such a wound dressing includes a support substrate for placement at a dermal wound. The support substrate may be of varied size to cover any portion of or the entirety of a dermal wound. In certain embodiments, support substrates may be in the form of a two dimensional sheet that overlays a dermal wound. In other embodiments, the support substrate is adapted to at least partially fill a wound opening, thereby providing a three dimensional wound dressing contacting wound edges and floor. FIG. 11 illustrates an exemplary wound dressing according to the invention placed in a dermal wound. The illustrated wound dressing includes a radial gradient of growth factor which promotes directional migration of cells into the wound site to facilitate improved wound healing.

Support substrates useful in the present invention possess cytocompatibility which means that the support substrate must not be cytotoxic to desired cells. Second, the support substrate must be biocompatible. Biocompatible means that a support substrate does not cause a significant immunological and inflammatory response when placed at the dermal wound and is preferably biodegradable affording non-toxic species.

The support substrate of the wound dressing may be made of a polymeric material. Useful polymeric materials for this purpose include, but are not limited to, polytetrafluoroethylene, polydimethylsiloxane, poly-vinylidine fluoride, polyethylene, polystyrene, polycarbonate, polyhydroxyethyl methacrylate, polyvinyl alcohol, polyvinyl chloride, polycaproamide, polyetheyleneoxide, polyethyleneterephthalate, polyacrylonitrile, silicones, polysilanes, polysiloxanes, polyurethanes, polylactides, polyglycolic acid, poly-beta hydroxybutyrate, polyepisilon caprolactone, polyanhyhdrides, polyorthoesters, polyiminocarbonates, mixtures thereof and copolymers thereof. In certain embodiments, the support substrate is made of an interpenetrating polymer network ("IPN") of at least two polymeric materials.

In yet other embodiments, the support substrate of the wound dressing is made of a hydrogel. Hydrogels useful in the present invention include, in general, naturally-derived hydrogels, semi-synthetic hydrogels and synthetic hydrogels. A particularly preferred hydrogel for use as a support substrate is a semi-synthetic derivative of hyaluronic acid which is sold under the tradename EXTRACEL (Glycosan Biosystems). An alternative hydrogel useful in the invention is available under the federally registered trademark HYAFF (Fidia Advanced Biopolymer s.r.l.). HYAFF materials are available in the form of fibers, membranes, microspheres and three dimensional matrices. Besides being non-cytotoxic and biocompatible, HYAFF is furthermore biodegradable. Synthetic hydrogels include materials described in U.S. Published Patent Application 2007/0128175, directed to the use of small peptides as gel scaffold building blocks via a self-assembly hydrogelation strategy. Common components of semi-synthetic or synthetic hydrogels include, e.g., polyvinyl alcohol, sodium polyacrylate, acrylate polymers and copolymers with an abundance of hydrophilic groups. Natural hydrogel materials include, e.g., agarose, methylcellulose, collagen, and hyaluronic acid (also termed hyaluronan or hyaluronate).

Certain other embodiments utilize a support substrate based on a natural product. Suitable natural products for this purpose include, for example, alginates, gelatins, collagen, cellulose, fibrin, hyaluronan, polycarbohydates, mycoses, polyxyloses, chitans, polymers of amino glucoses, tragacanths, and latexes.

Yet other embodiments include a support substrate prepared through the sol-gel process. Suitable sol-gel materials for use in the invention include the inorganic-organic hybrid ceramers described by Tian et al. (*Chem. Mater.*, 9 (4), 871-874, (1997)). The respective inorganic-organic hybrid ceramers are biomaterials endowed with biodegradable and biocompatible properties that favor wound healing. Such materials were demonstrated to be suitable supports for fibroblast cell culture with degradation profiles encouraging tissue invasion and reconstruction.

A wound dressing according to the invention further includes a growth factor gradient immobilized to the support substrate. In the case where the support substrate is provided substantially in the form of a sheet, the growth factor gradient is a two dimensional radial gradient cast in the desired shape to adequately cover the wound. In the case of wound-filling (i.e., three dimensional) support substrates, the growth factor gradient may be provided as a three dimensional gradient that decreases/increases in growth factor concentration in a preselected manner.

A wide variety of growth factors may be incorporated into the support substrate of the wound dressing, including, but not limited to, epidermal growth factor ("EGF"), insulin-like growth factor 1 ("IGF-1"), basic fibroblast growth factor ("bFGF"), platelet-derived growth factor ("PDGF"), vascular endothelial growth factor ("VEGF"), keratinocyte growth factor ("KGF"), transforming growth factor alpha ("TGF-a"), transforming growth factor beta ("TGF-b") and mixtures thereof.

In certain embodiments, the support substrate will further include an extracellular matrix protein, such as collagen, fibronectin, laminin, and, optionally, one or more angiogenesis factors such as matrix metalloproteinase ("MMP"), angiopoietins Ang1 or Ang2, or Delta-like ligand 4 ("Dll4").

Growth factors may be immobilized to the support substrate of the wound dressing by various methodologies known in the art, including but not limited to covalent linkage or high affinity interaction. Covalent linkages fabricated by the photochemical approach described herein are the preferred mode for immobilizing growth factors to support substrate.

Examples of covalent bonding chemistry useful in the present invention include those approaches in which bifunctional cross-linker molecules are used. The cross-linker molecules may be homo-bifunctional or hetero-bifunctional, depending upon the nature of the molecules to be conjugated. Homo-bifunctional cross-linkers have two identical reactive groups. Hetero-bifunctional cross-linkers are defined as having two different reactive groups that allow for sequential conjugation reaction. Various types of commercially available cross-linkers are reactive with one or more of the following groups: primary amines, secondary amines, sulphydryls, carboxyls, carbonyls and carbohydrates.

Examples of amine-specific cross-linkers are bis(sulfosuccinimidyl) suberate, bis [2-(succinimidooxycarbonyloxy)ethyl]sulfone, disuccinimidyl suberate, disuccinimidyl tartarate, dimethyl adipimate-2 HCl, dimethyl pimelimidate-2 HCl, dimethyl suberimidate-2 HCl, and ethylene glycolbis[succinimidyl-[succinate]]. Cross-linkers reactive with sulfhydryl groups include bismaleimidohexane, 1,4-di-[3'-(2'-pyridyldithio)-propionamido)] butane, 1-[p-azidosalicylamido]-4-[iodoacetamido]butane, and N-[4-(p-azidosalicylamido) butyl]-3'-[2'-pyridyldithio] propionamide. Cross-linkers preferentially reactive with carbohydrates include azidobenzoyl hydrazine. Cross-linkers preferentially reactive with carboxyl groups include 4-[p-azidosalicylamido]butylamine.

Heterobifunctional cross-linkers that react with amines and sulfhydryls include N-succinimidyl-3-[2-pyridylditlio] propionate, succinimidyl [4-iodoacetyl]aminobenzoate, succinimidyl 4-[N-maleimidomethyl]cyclohexane-1-carboxylate, m-maleimidobenzoyl-N-hydroxysuccinimide ester, sulfosuccinimidyl 6-[3-[2-pyridyldithio]propionamido]hexanoate, and sulfosuccinimidyl 4-[N-maleimidomethyl]cyclohexane-1-carboxylate. Heterobifunctional cross-linkers that react with carboxyl and amine groups include 1-ethyl-3-[[3-dimethylaminopropyl]-carbodiimide hydrochloride. Heterobifunctional cross-linkers that react with carbohydrates and sulfhydryls include 4-[N-maleimidomethyl]-cyclohexane-1-carboxylhydrazide-2 HCl, 4-(4-N-maleimidophenyl)-butyric acid hydrazide-2 HCl, and 3-[2-pyridyldithio]propionyl hydrazide. The cross-linkers are bis-[(3-4-azidosalicylamido) ethyl]disulfide and glutaraldehyde. Amine or thiol groups may be added at any polypeptide so as to provide a point of attachment for a bifunctional cross-linker molecule.

Particularly preferred crosslinkers useful in the preferred photochemical approach are ANB—NOS(N-5-Azido-2-nitrobenzoyloxysuccinimide), Sulfo-SAND(Sulfosuccinimidyl 2-[m-azido-o-nitrobenzamido]ethyl-1,3'-dithiopropionate), SANPAH(N-Succinimidyl-6-[4'-azido-2'-nitrophenylamino]hexanoate) and Sulfo-SANPAH (Sulfosuccinimidyl-6-[4'-azido-2'-nitrophenylaminio]hexanoate) which are heterobifunctional crosslinkers that contain an amine-reactive N-hydroxysuccinimide (NHS) ester and a photoactivatable nitrophenyl azide. NHS esters react efficiently with primary amino groups ($—NH_2$) in pH 7-9 buffers to form stable amide bonds. When exposed to UV light nitrophenyl azides form a nitrene group that can initiate addition reactions with double bonds, insertion into C—H and N—H sites, or subsequent ring expansion to react with a nucleophile (e.g., primary amines). The latter reaction path dominates when primary amines are present.

In a preferred method for immobilizing the growth factor on the support substrate, recombinant growth factor is rendered photoactive via conjugation to a photactivatable crosslinker. A particularly preferred photoactivatable heterobifunctional crosslinker is Sulfo-SANPAH which contains an amine-reactive N-hydroxysuccinimide (NHS) ester and a photoactivatable nitrophenyl azide. Photoreactive growth factor is synthesized via the reaction of one or more functional groups with the bifunctional crosslinker. For example, photoreactive EGF may be obtained via the reaction of primary amine groups of EGF with the N-hydroxysuccinimide functionality of Sulfo-SANPAH. This exemplary reaction may be completed under mild conditions such as, for example, pH 8.4, HEPES buffered saline, for 8 hours at room temperature with gentle shaking and a 50-fold molar excess of crosslinker in order to insure that a maximum amount of EGF is rendered photoactive.

Subsequent synthesis and purification steps are then performed in the dark to preserve the photoactive moiety on the photoactive crosslinker. Growth factor gradient immobilized to a support substrate is then prepared generally as follows: photoactive growth factor is photoimmobilized onto a support substrate via the photoactive functionality of the bifunctional crosslinker. For example, EGF coupled to sulfo-SANPAH may be immobilized onto a polystyrene surface, or a matrix of hyaluronic acid-based hydrogel such as EXTRACEL via the phenyl azide functionality of the coupled sulfo-SANPAH. This surface-immobilization step may optimized in a routine manner by altering parameters such as photoactive moiety, UV exposure intensity and exposure duration. To create two dimensional surfaces patterned with gradients of growth factor, standard photoimmobilization techniques may be utilized in combination with a gradient-patterned photomask film. For example, gradient images may be created in Adobe Illustrator 10, and then used to print photomask transparency films. The slope of the gradient may be controlled via alterations and photomask pattern design. Such an approach was used by the present inventors to generate a variety of gradient patterns for the migration studies described herein, including gradient patterns following the power law equations of $y=0.3092x^{1.5608}$ and $y=4.5806x^{0.9869}$ in units of grayscale intensity versus pixels.

The photoactive growth factor may then be contacted with the substrate surface and allowed to dry in place. For example, a solution of EGF conjugated to sulfo-SANPAH may be pipetted onto a polystyrene surface or a hydrogel matrix may be immersed in the solution. The surface or matrix may then be subsequently dried by, for example, drying in an oven at approximately 40° Centigrade. Use of a hydrogel matrix makes the drying step optional as tethering of the EGF molecule is not dependent on drying. The dried support substrates may then be covered with film photomask with varied gradient slopes, prepared as described above, and subsequently exposed to ultra-violet light at 365 nm wavelength and 90 $mW\backslash cm^2$ for 120 seconds. Upon UV exposure, the photoactive group of the bifunctional crosslinker enables the immobilization of the photoactive growth factor to the support substrate. In the case of EGF conjugated to sulfo-SANPAH, the nitrophenyl azide forms a nitrene group that can initiate additional reactions with double bonds, insertion reactions into C—HN—H sites, or subsequent ring expansion to react with a nucleophile (e.g., primary means). Substrate surfaces so treated may then be rinsed with solvent (e.g., $diH_2O$) to remove free growth factor. To prepare for placement at a dermal wound or for cell seeding, support substrates including immobilized growth factor gradients may be subjected to sterilization by, e.g., UV light.

The preferred photochemical system described herein for the creation of patterned materials that induce directed cell migration has numerous advantageous features. First, the immobilizing (also termed "tethering") chemistry is performed under mild conditions, thus retaining excellent growth factor bioactivity. Regarding the inventors' exemplary system, it had been shown previously[39] that a lysine free variant of human EGF ("hEGF") has the same binding activity as wild type hEGF, showing that the residues known to be involved in EGF binding to its receptor do not include the lysine groups; thus, conjugation of SS to the lysine groups in EGF did not interfere with its binding to EGF receptor. Regarding the sustained bioactivity of immobilized EGF, migration results indicated that the patterned EGF that had not yet interacted with cells remained active for the duration of the experiment. The stability of various growth factor gradient patterns to withstand many days of rinsing and incubation with culture media in the absence of cells has been confirmed by the inventors.

The preferred immobilization scheme may also be applied to numerous other extracellular matrix ("ECM") components, growth factors, angiogenesis factors and biomaterial scaffolds. In broad terms there are three major components of the ECM: fibrous elements (e.g., collagen, elastin or reticulin); link proteins (e.g., fibronectin, laminin); and space filling molecules (e.g., glycosaminoglycans). Any one or more ECM components described herein or known in the field may be incorporated onto/into the support substrate.

It is important to note that polystyrene was utilized by the inventors simply as a model support substrate upon which the concept of gradient patterning and directed cell migration could be developed and tested. Specific examples described herein are therefore non-limiting and, e.g., tethering techniques presently described are broadly applicable to numerous other biomaterials that may be more or less suitable as wound-healing support substrates. The technique of growth factor patterning not only allows the construction of platforms that enable control over cell functions, such as directed migration, but it is also biologically relevant, as many growth factors in vivo are presented to cells in a matrix-bound form.[40-42]

Noncovalent methods of conjugation may also be used. Noncovalent conjugation includes hydrophobic interactions, ionic interactions, high affinity interactions such as biotin-avidin and biotin-streptavidin complexation and other affinity interactions. In one embodiment, a molecule such as avidin is attached to a linking molecule such as Sulfo-SANPAH. This conjugate, once attached to a support substrate according to the invention, then becomes a universal linking moiety for any agent (e.g., growth factor) attached to a biotin molecule.

As noted above, patterned gradient wound dressings according to the invention are characterized by a growth factor concentration across the growth factor gradient defined by a mathematical formula such as a power ($y=ax^b$), $\log(y=a \ln(x)+b)$ or linear ($y=mx+b$) equation. In a particularly preferred embodiment of the invention, the growth factor gradient is characterized by an exponentially increasing concentration of growth factor along one of its dimensions. An exponentially increasing concentration of immobilized growth factor was demonstrated by the inventors to yield an unexpected improvement in the promotion of directed cell migration across the growth factor gradient.

In a preferred embodiment, a wound dressing is provided that includes a growth factor gradient comprising immobilized EGF where the low to high EGF concentrations across the growth factor gradient range from 0 ng/cm$^2$ to about 36 ng/cm$^2$, more preferably, from 0 ng/cm$^2$ to about 9 ng/cm$^2$.

In preferred embodiments of two or three dimensional wound dressings, the wound dressing includes a growth factor gradient that is spatially-oriented relative to the support substrate such that the low concentration portion of the growth factor gradient is located along a periphery of the support substrate. Such orientation provides that the low concentration of the growth factor gradient is immediately adjacent to the dermal wound edge when the wound dressing is placed at a dermal wound and, further, the high concentration of growth factor is spaced apart from and separated by the gradient from the wound's edge and floor.

In certain such embodiments, a patterned gradient is provided in a radial pattern. Accordingly, radial patterned gradients may be fabricated to vary in concentration in two dimensions or, alternatively, three dimensions. In certain preferred embodiments, the patterned gradient is provided in a radial pattern in which the concentration of growth factor present in the gradient decreases along a straight line that runs from the central point of a wound dressing to the outside edge of the dressing. In other embodiments, the radial pattern decreases in concentration from a pre-selected point of a wound dressing, not necessarily the central point, along a straight line to the outside edge of the dressing. The preferred photopatterning method described herein allows the artisan to prepare such radial patterns and minor variations thereof.

The inventors' results obtained from their exemplary system indicated that photo-immobilized gradients of EGF induce accelerated and directed migration of keratinocytes. Net migration of cells in a single direction occurred at a rate that was five-fold greater than that of cells on control surfaces. Moreover, the tethered EGF remained biologically active for a minimum of several weeks, in comparison with the 0.5-2 hours half-life of untethered EGF.[35-37]

The inventors also showed that the cells responded to a remarkably small concentration of EGF (FIG. 4), which is, in fact, many fold smaller than the amount of untethered EGF needed to elicit keratinocyte migration in other studies.[38] As the inventors' studies were carried out in serum free medium, the only growth factor to which the cells were exposed was the tethered EGF. Through negative control conditions and irreversible blocking of the EGF receptor, the inventors demonstrated that the migration behavior observed on patterned surfaces was due to specific interactions of keratinocytes with tethered EGF. Immunocytochemical staining for a proliferation marker (proliferating cell nuclear antigen [PCNA]) confirmed that the advancement of the leading cell edge quantified in FIGS. 5 and 6 was indeed due to cell migration and not attributable to advancement purely via culture expansion (data not shown).

The migration rates the inventors observed in their model system at each individual time point were not statistically different between 35% and 65% gradient conditions following power-law curve fits (power of 0.7369 for the 65% and power of 1.6554 for the 35% gradient) but a significant difference in rates did emerge when evaluating across the first 13 days of migration (before the gradients converged on the same EGF concentration). The cells thus preferred to migrate on a gradient where the EGF levels increased slowly at first, followed by steepening of the gradient slope, rather than on a gradient that displayed rapid increases in EGF levels at the beginning of the gradient. The inventors found that for gradients that had much higher EGF concentrations near the cell-seeding site, the cells experienced an initial spurt of migration, and then stopped migrating. As described herein, the system used by the inventors for gradient generation provides many possibilities with respect to the type and slope of gradients that can be created.

While recent studies have confirmed the ability of growth factors (including EGF) immobilized via other methods to stimulate cell migration;[41,43,44] the inventors' system exhibits several advantages over these investigations. Namely, precise control over growth factor spatial patterns on a cellular scale distinguishes the photo-patterning method from the electrophoresis gradient-maker technique previously described,[41,44] and it is this degree of control afforded by the present guidance that allows the artisan to utilize systematic variations in growth factor gradient slope to affect the speed and direction of cell migration. Because other immobilization methods have not been amenable to fine-tuning of the precise location of growth factor presentation, these methodologies have not addressed how alterations in gradient slope impact cell migration, thereby making further exploration and optimization of immobilized growth factor-induced directed migration difficult.

To better explain and demonstrate the flexibility and potential of the present approach, the inventors have fabricated numerous other gradient patterns beyond those specifically described in the examples section; the range of gradient patterns that the inventors have made is shown in Table 1. The mathematical descriptions of gradient patterns listed in Table 1 illustrate the excellent level of immobilization control enabled by the present system and the large array of gradient pattern types and slopes that can be achieved. The importance of precisely controlling gradient slope is verified by the inventors' results, as they have shown that immortalized human keratinocytes (HaCaTs) on gradients with a gradually increasing EGF concentration slope migrated significantly faster than HaCaTs on gradients whose EGF concentration slopes gradually decreased.

TABLE 1

Mathematical description of synthesized gradient patterns (in grayscale intensity vs. pixels)

| Linear | Power | Logarithmic |
|---|---|---|
| y = 3.4732x − 1.8789 | y = 0.3092x$^{1.5608}$* | y = 77.592Ln(x) − 34.894 |
| y = 5.6247x − 5.2273 | y = 4.5806x$^{0.9869}$* | y = 70.41Ln(x) + 0.5326 |
| y = 5.9852x − 3.4962 | y = 20.587x$^{0.6407}$* | y = 92.34Ln(x) + 0.6636 |
| y = 6.1871x + 1.2 | y = 0.1523x$^{1.9196}$* | |
| y = 7.4083x − 0.6368 | y = 0.0002x$^{3.6471}$* | |
| y = 10.231x + 2.7692 | | |

*Indicates gradient patterns reported in cell migration results (see Examples).

Moreover, the patterning itself was accomplished with a minimum of materials and tools, in comparison with the complex microfluidic gradient schemes that have been recently described[45,46] Also, the present photopatterning method makes efficient use of small amounts of growth factor by tethering only to a surface (if desired), and has the potential to be easily scaled up.

Multiple different gradients cannot be made simultaneously using the electrophoresis gradient-maker technique,[41,44] whereas the present system can be expanded to make large arrays of numerous photopatterned growth factor gradients. Another unique capability of the present photo patterning system is that multiple proteins or growth factors may be immobilized to create multiple different patterns. As wound healing involves a complex array of ECM and growth factor signals at various concentrations, combining EGF patterns with other biological signals is certainly possible—in the same gradient, different gradient, constant concentration—simply by applying a different photomask and the desired photoactive growth factor solution. Such materials also enable a multiplexed analysis of how different growth factor combinations affect cell migration.

The present invention is envisioned to encompass construction of complex, gradient-patterned 3D structures. Using layer-by-layer photolithographic techniques, such as living radical photopolymerization,[47] the present methods may certainly be applied to construct 3D support substrates, termed "scaffolds", that extend radial gradients in all directions, such that cell migration is encouraged from the underlying wound bed in addition to the wound edges. 3D photopatterning may also be accomplished by initiating photoactive biomolecule tethering through photomasks placed on top of transparent hydrogel scaffolds. In this procedure, hydrogels would be loaded with photoactive biomolecules (either prior to or after hydrogel formation), and the photoactive molecules would be covalently tethered in a specified gradient pattern after application of the photomask and exposure to UV light. Biomolecules would not be immobilized in areas that were not exposed to light, and such untethered molecules would be removed with washing.

As can be appreciated, the methods described herein encompass complex wound-healing systems that include the incorporation and synergism of multiple immobilized and patterned biomolecules, the targeting of multiple cell types (i.e., addition of dermal fibroblasts), and translation to a wide variety of support substrate geometries. For example, the following examples section describes a radial patterned gradient of immobilized EGF The present invention further contemplates a method for treating a dermal wound using the patterned gradient wound dressings described and claimed herein during the course of wound management. Dermal wounds to be treated by the present methods include acute dermal wounds. For example, EGF may be applied to a fire victim's burn wounds to speed up the process of re-epithelialization. As well, chronic wounds, such as diabetic ulcer or bed sores, may be treated via dressing of the present invention. Chronic wounds are a particularly important area for application of the present invention as chronic wounds are often characterized by a lack of growth factors which leads to increased complications in healing. Dressings according to the invention are certainly envisioned to be, in certain embodiments, multi-modal in nature where drug/antibiotic entities are co-delivered to the wound site via the dressing.

Yet another aspect of the invention provides a method of screening for agents that promote directed cell migration. Such a method includes steps of: (a) providing a support substrate and a test agent gradient immobilized to the support substrate; and (b) evaluating the ability of cells to migrate across the test agent gradient and comparing to a control that is treated with the same conditions but without the test agent gradient. An improvement in migration of cells across the test agent gradient relative to control indicates that the test agent promotes directed cell migration.

Assay methods preferably use a two dimensional sheet of polymeric material, preferably polystyrene as described in the examples section, to conduct migration evaluation. The test agent gradient is preferably characterized by an exponentially increasing concentration of test agent across the test agent gradient from low to high test agent concentrations whereby the cells are evaluated for their ability to migrate from low to high test agent concentrations. However, it is certainly possible that gradients fitting other mathematical formulas may be useful alone or in combination in the context of screening assays. Based upon the model system and methodology described in detail in the examples section, the artisan may test agents for the example growth factor to provide screening systems for identifying agents capable of directing cell migration. While a wide range of biological and small molecule entities may be screened in the present methods, exemplary target families include growth factors, cytokines, chemokines, EGF receptor agonists and derivatives/analogs thereof.

The following examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

III. Examples

Example 1

Materials and Methods

All chemicals were obtained from Sigma-Aldrich (St. Louis, Mo.) unless otherwise noted.

Cell culture. Immortalized human keratinocytes (HaCaTs, courtesy of N. Fusenig, DKFZ, Heidelberg, Germany) were cultured and maintained in Dulbecco's modification of eagle's medium (DMEM), 10% fetal bovine serum (FBS), 1% glutamine, and 1% penicillin/streptomycin at 37° C., 5% CO2.

Figure 1:
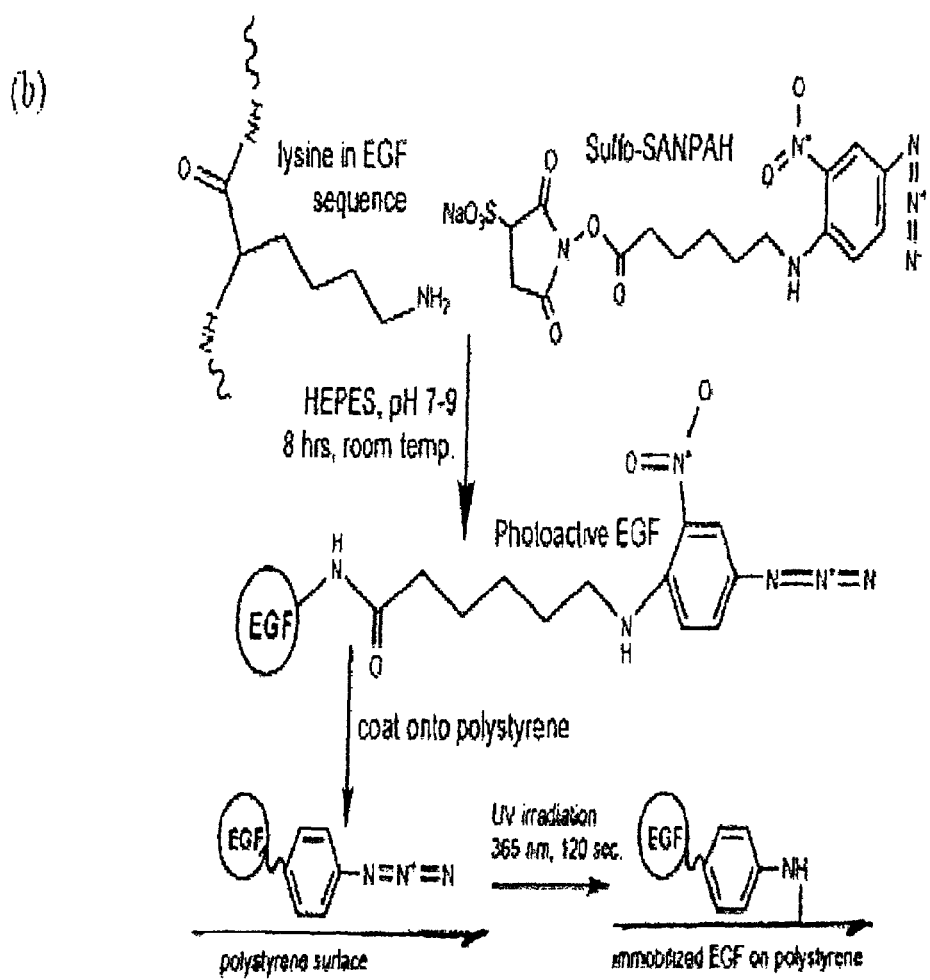
FIG. 1. (A) Human epidermal growth factor (hEGF) amino acid sequence (SEQ ID NO:1). Each hEGF contains 53 amino acids, including two lysines (K) at positions 28 and 48[35]. (B) Reaction scheme of SS with primary amines of EGF to form photoactive EGF, and subsequent photoimmobilization of photoactive EGF onto a polystyrene surface. SS, sulfosuccinimidyl-6-[40-azido-20-nitrophenylamino]hexanoate.

EGF modification. Recombinant human EGF (Peprotech Inc., Rocky Hill, N.J.) having the amino acid sequence of SEQ ID NO:1 (see FIG. 1) was rendered photoactive via conjugation to Sulfo-SANPAH (sulfosuccinimidyl-6-[40-azido-20-nitrophenylamino]hexanoate; Pierce Biotechnology Inc., Rockford, Ill.). Sulfo-SANPAH (SS) is a heterobifunctional crosslinker containing a photosensitive phenyl azide group on one end and an amine-reactive N-hydroxysuccinimide on the other (FIG. 1). Photoreactive EGF was synthesized via the reaction of primary amine groups of EGF with the N-hydroxysuccinimide functionality of SS. The coupling reaction of EGF with SS was performed in HEPES buffered saline, pH 8.4, for 8 hours at room temperature with gentle shaking and a 50-fold molar excess of SS in order to ensure that a maximal amount of EGF was rendered photoactive. All synthesis and purification steps were performed in the dark to preserve the photoactive moiety on SS. The formation of SS-EGF was verified spectrophotometrically (Beckman DU530 UV/Vis Spectrophotometer).

Creation of EGF gradients. In an adaptation of previous methods EGF was photoimmobilized onto polystyrene plates via the phenyl azide functionality of the coupled SS[29]. This surface-immobilization process was optimized in the inventors lab by altering parameters such as photoactive moiety, UV exposure intensity and duration, and surface chemistry using a model protein, bovine serum albumin (BSA) (data not shown), which was later replaced with EGF. In order to create 2D surfaces patterned with gradients of EGF, standard photoimmobilization techniques were used in combination with a gradient-patterned photomask film. Several 3×18 mm gradient images were created in Adobe Illustrator 10, and were then used to print photomask transparency films (Silverline Studios, Madison, Wis.). The slope of the gradient was controlled via alterations in photomask pattern design; the two gradient patterns generated for the following migration studies followed the power law equations of $y=0.3092x^{1.5608}$ and $y=4.5806x^{0.9869}$ in units of grayscale intensity vs. pixels.

Silicone isolators (Grace Bio-Labs Inc., Bend, Oreg.) were placed onto tissue culture polystyrene (TCPS) dishes, and 110 μL of SS-EGF solution (0.17 μg/mL) was pipetted into one isolator on each dish and allowed to dry in an oven at 40° C. The unconjugated SS control was quenched with Tris buffer and plated in the same manner. The dried SS-EGF was then covered with film photomasks with varied gradient slopes. All samples, including TCPS controls with no SS-EGF, were exposed to ultraviolet light at 365 nm wavelength and 90 mW/cm$^2$ for 120 seconds (Novacure 2001, EXFO UV Curing, Mississauga, Ontario, Canada). Upon UV exposure, the phenyl azide group enables immobilization of the SS-EGF to the dish as illustrated in FIG. 1 and described previously.[28] Spectroscopy was used to determine the optimal UV exposure time for complete photolysis of SS. All plates were rinsed twice with deionized water (diH$_2$O) and then filled with diH$_2$O to rinse overnight on an orbital shaker (30 r.p.m.). To prepare for cell seeding, the plates were UV sterilized in a laminar flow hood for 1 hour.

Gradient characterization. To verify that EGF was successfully immobilized in a gradient pattern, EGF was fluorescently labeled with fluorescein (FITC) using a commercial kit (Sigma-Aldrich), conjugated to SS, and then used to create a gradient of immobilized SS-EGF-FITC using the method described above. Photomicrographs were taken at 10 equally spaced intervals at 200× magnification (Olympus IX51 microscope with epifluorescence, Hamamatsu 285 digital camera, and Simple PCI digital imaging software [Compix Inc. Imaging Systems, Cranberry Township, Pa.]). ImageJ software was used to measure fluorescence intensity every 2 μm along the gradient path length, at six different points along the gradient path width. These data were plotted against gradient path length.

A modified ELISA for hEGF (Peprotech Inc.) was used to quantitatively determine the average total immobilized EGF (ng/cm$^2$) on the gradient patterns. Briefly, immobilized EGF was detected via standard immunochemical methods using biotinylated rabbit anti-hEGF, avidin-labeled HRP, and ABTS (2,20-Azino-bis(3-ethylbenzothiazoline-6-sulfonic acid)) liquid substrate solution as the chromogenic substrate, followed by reading absorbance at 405 nm (Bio-tek Synergy HT plate reader). A calibration curve was constructed using the capture antibody-coated plate (rabbit anti-hEGF) and untethered hEGF provided with the kit, in combination with the same detection molecules described above. The ELISA was also performed on negative controls consisting of unpatterned TCPS or patterned SS without EGF.

Migration studies and analysis. HaCaTs were seeded at 5×10$^5$ cells/mL in 1 cm$^2$ removable wells in reduced-serum medium (5% FBS) at the start of each gradient pattern (for all samples including controls of SS and TCPS). Unpatterned controls consisted of unmodified TCPS, wherein an outline of the same size as the EGF patterns was traced on the plate, and HaCaTs were seeded within 1 cm$^2$ removable wells at the base of the "empty" outline under identical conditions as patterned samples (5×10$^5$ cells/mL, 5% FBS medium). Grid-patterned transparencies were attached underneath the patterned surfaces in order to facilitate tracking cell movement. After allowing 24 hours for cell attachment, the reduced serum medium was replaced with serum-free medium and the seeding fences were removed, thus allowing the cells to access the gradient patterns. Photomicrographs were taken of the leading edge of cell migration at 12.5× magnification every 24 hours for 16 days. To verify that migration was due to specific interactions of cells with the tethered EGF, the experiment was repeated adding an irreversible EGF receptor blocker (PD168393; EMD Biosciences Inc., San Diego, Calif.) to the medium at different time points during the migration study.

Net cell edge displacement in a single direction was measured by overlaying time-course images (Adobe Photoshop Elements 2.0), and then quantifying migration distance (NIH ImageJ) via measurement of advancement of the leading cell edge. Using ImageJ software, the leading edge of HaCaTs was carefully traced and copied, along with portions of the micrograph underneath, onto the next time-point micrograph. Grid lines were used to line up the micrographs precisely. The migration distance of the advancing cell sheet was measured at five separate locations on each sample by drawing perpendicular lines between the previous leading edge and the new leading edge at equally spaced intervals, with a minimum sample size of three per condition.

Following the end of migration experiments, cells were lysed in mammalian cell extraction buffer (M-PER, Pierce Biotechnology Inc.) and the lysate was removed from the plates. To quantify the amount of EGF remaining immobilized to the plates, surfaces were washed in phosphate-buffered solution (PBS), and an EGF ELISA was performed as described in an earlier section.

Statistics. All experiments were performed a minimum of three separate times, with n greater or equal to 3. Data were compared using two tailed, unpaired t-tests. P values less than or equal to 0.05 were considered to be statistically significant. Data are presented as mean +/−standard deviation.

Example 2

EGF Modification

Figure 2:
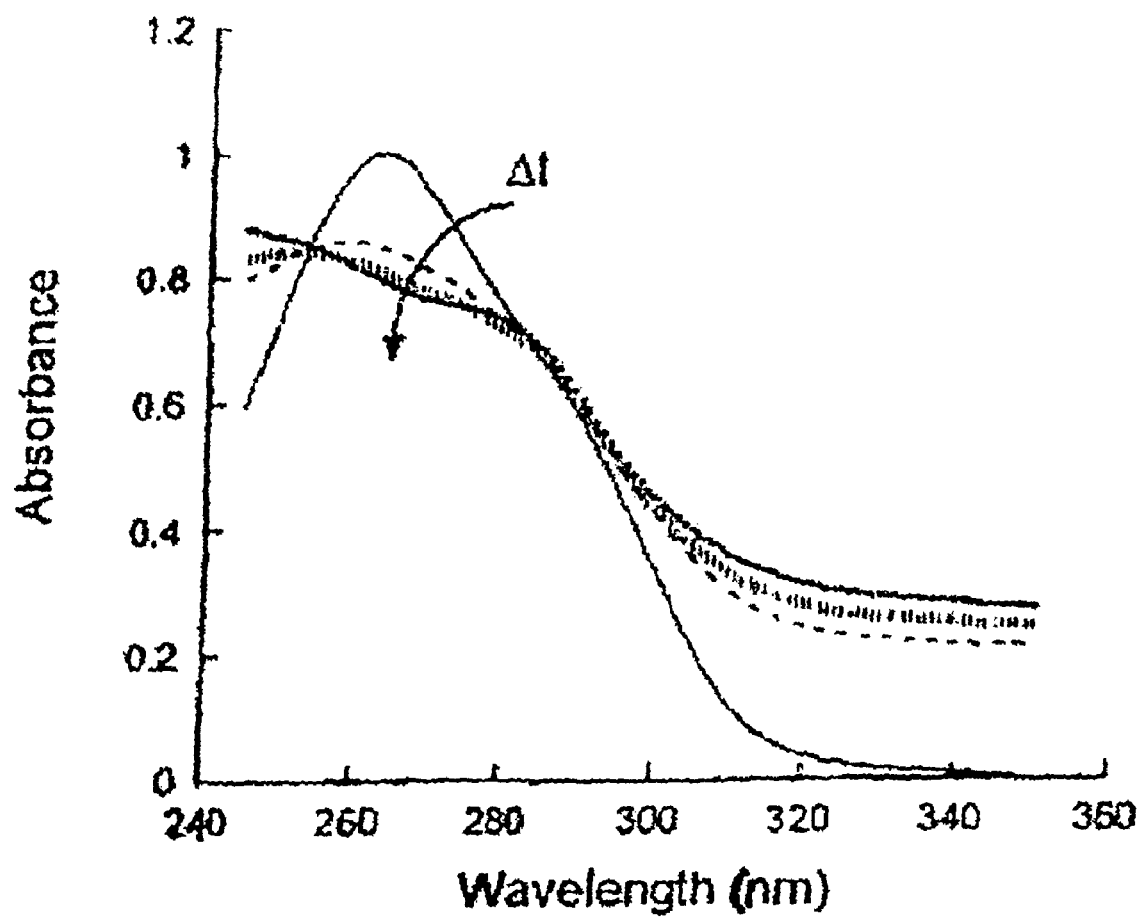
FIG. 2. Absorbance spectra confirm conjugation of SS to EGF, and optimal time for photolysis of phenyl azide on SS.

Spectroscopy was used to confirm conjugation of SS to EGF, as well as determine the optimal UV exposure time for complete photolysis (i.e., tethering) of the SS. Conjugation of SS to EGF was confirmed by an absorption spectrum displaying peaks at 262 nm (corresponding to the photoactive phenyl azide of SS) and 280 nm (corresponding to EGF). Owing to the breadth of the 262 nm peak and the coupling of multiple SS groups to a single EGF molecule, the EGF peak appears as a shoulder, rather than as an isolated peak (FIG. 2). To optimize the UV exposure time needed for photolysis of the phenyl azide (and hence covalent tethering to our surface), the disappearance of the 262 nm peak was measured as a solution of SS-EGF was exposed to UV light for varying amounts of time. The loss of the phenyl azide peak of SS upon UV exposure is a standard measure of phenyl azide photolysis.[30, 31] Within 1 minute of UV exposure, the peak dropped dramatically, indicating partial photolysis of SS. At 2 minutes, the photolysis appeared to have reached a maximum, and remained relatively unchanged at 5 minutes. The 280 nm shoulder corresponding to EGF remained as photolysis progressed (FIG. 2).

Example 3

Gradient Characterization

Photo-immobilization of fluorescently labeled SS-EGF to polystyrene plates via the phenylazide functionality of SS was successfully completed in the desired gradient pattern (FIG. 3). The actual slope of the EGF gradient (as measured by image quantification) correlated well with the predicted gradient slope (i.e., the gradient slope of the photomask). Immobilized EGF increased steadily along the length of the gradient path (i.e., along the x-axis), while remaining homogeneous across the width of the path (i.e., along the y-axis), as desired (FIG. 3).

An ELISA for hEGF yielded a quantitative description of the total amount of EGF tethered across each gradient pattern. Combining this information with gradient intensity curves, the concentration of EGF at any point along the gradient can be calculated. FIG. 4 illustrates the experimentally calculated EGF concentration at a few example points along the gradient paths used in the cell migration experiments. As shown in FIG. 4, the concentrations of tethered EGF were extremely small, with values <10 ng/cm$^2$. The EGF concentration was equal on both gradients at a distance of approximately 13.5 mm, which proved significant for migration calculations discussed in the following sections. Also shown in FIG. 4 are the equations and curve fits for the EGF concentration vs. distance from gradient start, as well as plots of the EGF concentration values for each gradient. For ease of reading and identification, the gradient in FIG. 4A will be referred to as the 65% gradient, while the gradient in FIG. 4B will be referred to as the 35% gradient. Both gradients closely follow power-law curve fits (power of 0.7369 for the 65% gradient, power of 1.6554 for the 35% gradient). In general terms, the slope of the 65% gradient gradually decreases with distance from the start of the gradient, meaning that the cells initially contact rapidly rising levels of EGF, but then experience smaller increases in EGF as they progress up the gradient. Conversely, in the 35% gradient, the slope gradually steepens with distance, meaning that the cells initially contact levels of EGF that increase slowly, followed by more rapid increases in EGF levels as they migrate up the gradient.

Example 4

Migration Experiments and Analysis

As shown in FIG. 5, the unidirectional migration speed of HaCaTs on immobilized gradients of SS-EGF (both 65% and 35% gradients shown in FIG. 4) was approximately five-fold greater than on the TCPS and SS controls (p<0.001 for all time points >Day 0). As noted earlier, migration experiments were performed in the absence of serum and media growth factor supplements, with the tethered EGF thus comprising the only growth factor source. The cells migrated as a sheet, which is consistent with previously published wound-healing theories and keratinocyte migration models.[32] While the migration rate of keratinocytes on the 35% gradient was consistently higher than that of cells on the 65% gradient, this difference was not statistically significant at any individual time point. However, the average migration rate of cells on 35% gradients was statistically higher than that of cells on 65% gradients when averaged across multiple time points, specifically Days 1-13 of the experiment (44.1+/−3.6 mm/hours vs. 39.8+/−3.9 mm/hours; p<0.01). As noted in a previous section and in FIG. 4, the EGF concentration values on the two gradients converge at a distance of 13.5 mm. The cells on EGF gradients reach this distance between Days 13 and 14, thus providing the rationale for averaging the migration speed up to Day 13 in order to accurately analyze statistical differences between the migration rates of cells on the two different gradients. The average migration rates over the entire course of the experiments (Days 0-16) correspond to the slopes of the linear fits of FIG. 5B, as summarized by Table 2.

TABLE 2

Linear fit equations for FIG. 5B, representing cumulative migration distance (mm) vs. time (days) for HaCaTs migrating on different surfaces

| Condition | Trendline equation | R$^2$ Value |
| --- | --- | --- |
| TCPS | y = 0.0917x | 0.9207 |
| SS | y = 0.1973x | 0.9615 |
| 35% SS-EGF | y = 1.0487x | 0.9963 |
| 65% SS-EGF | y = 0.956x | 0.9929 |

SS, sulfosuccinimidyl-6-[40-azido-20-itrophenylamino]hexano-ate;
EGF, epidermal growth factor;
TCPS, tissue culture poly-styrene;
HaCaTs, human keratinocytes.

The amount of EGF remaining on the migration surfaces following cell migration to the end of the gradients was also quantified in order to examine conservation of the immobilized EGF following interaction with cells. There was no significant difference in the total amount of EGF remaining on the two types of gradients when compared against each other: 7.42+/−4% for 35%, and 4.3+/−1.7% for 65% (p>0.05), with data expressed as a percentage of the original total amount of tethered EGF on corresponding pattern schemes before cell seeding. Other groups have documented that HaCaTs do not express EGF mRNA,[33] indicating that the postmigration EGF assay quantified only the photopatterned EGF.

Blocking the EGF receptor (EGFR) with PD168393 confirmed that the observed increase in HaCaT migration on EGF-patterned surfaces was directly attributable to the cellular recognition of immobilized EGF. First, by seeding HaCaTs on EGF-patterned and negative control surfaces in the presence of PD168393, it was verified that PD168393 did not alter cell adhesion. While PD168393 did not affect the ability of the cells to adhere to the surfaces, these cells never migrated, thus illustrating the importance of EGF-specific recognition in controlling migration in our system. In separate studies, PD168393 was added to HaCaTs on EGF gradients and negative controls during migration experiments (Day 5 or 10). The cells on EGF gradients abruptly stopped migrating within hours of adding PD168393, and never resumed migration (FIG. 6). Again, these results provide direct evidence that the migration trends observed in this system are EGF specific.

Example 5

Varying EGF Concentration

This example describes the effects on cell migration of varying concentration of photoactive growth factor during gradient pattern preparation. Photopatterning and cell migration analyses were carried out substantially as described in previous examples, except that the concentration of photoactive EGF solution contacted with the polymeric substrate was varied. FIG. 7 provides four graphs of cumulative cell migration (mm) plotted against time (days) for immobilized gradients prepared with the indicated photoactive EGF solutions. All gradient patterns were made with a 35% ([g2]) gradient mask.

The data indicate that cells migrated significantly further on gradients patterned using 167 µgEGF/ml than 83 µgEGF/ml and TCPS controls. The cumulative migration distance for 167 µgEGF/ml is significantly higher than 667 µgEGF/ml on days 6 and 7. The data for 667 µgEGF/ml shows a downward trend indicating a slowing migration speed after day 3. No significant difference in cumulative migration between 167 µgEGF/ml and 333 µgEGF/ml is observed, thereby indicating that there is no advantage to using twice the concentration of photoactive EGF during the photopatterning process.

Example 6

Radial and Rectangular Gradients of Photo-Immobilized Growth Factors Direct Keratinocyte Migration This example describes the development and testing of a radial gradient pattern of immobilized EGF by the inventors. This example also demonstrates the concurrent use of two different growth factor types immobilized to form a rectangular patterned gradient. Insulin-like growth factor-1 (IGF-1) is a fibroblast-derived growth factor that enhances keratinocyte migration by a mechanism that is distinct from that of EGF; specifically, IGF-1 stimulates cell membrane protrusion and spreading [48], which may be useful for sensing the immobilized growth factor gradients. Combination of IGF-1 with EGF in solution results in additive effects on wound reepithelialization [49]. Accordingly, this example describes a gradient of surface-immobilized EGF, combined with IGF-1, a factor that works synergistically with EGF, to provide a patterned gradient that induces directed migration of keratinocytes, promoting accelerated dermal wound healing.

The photo-reactive heterobifunctional cross-linker Sulfo-SANPAH(SS) was conjugated to EGF and IGF-1 (both 150 ng/µl) and then photo-immobilized onto tissue culture polystyrene (TCPS) using film photomasks with radial (EGF) or rectangular (EGF, IGF-1) gradients. The film photomask for the radial (EGF) pattern is depicted in the micrograph of FIG. 10. The micrograph shows the 20% gradient ([g1]) photomask film having a pattern with rapidly increasing slope approaching the center. The pattern gradually has fewer black dots and more transparent area with the center completely transparent. The transparent area allows UV light to travel through to the substrate, creating a gradient pattern of immobilized molecules with the highest surface density in the center. The rectangular gradients were also used to compare two different slope rates: [g1], a more rapidly increasing slope, and [g2], a slower increasing slope. More specifically, g1 conforms to the equation $y=0.0435x^2-1.0982x+9.8063$ and g2 conforms to $y=0.3092x^{1.5608}$. Unpatterned TCPS acted as a negative control. All samples were exposed to ultraviolet light (Novacure; 365 nm 90 mW/cm$^2$) for 120 seconds. Immortalized keratinocytes (HaCaTs, courtesy of N. Fusenig, DKFZ, Germany) were seeded at $5 \times 10^5$ cells/ml in 1 cm$^2$ temporary wells at the 'start' of each rectangular gradient pattern, or outside of a 1 cm$^2$ diameter cylinder of PDMS covering the radial gradients. The cells were allowed to attach for 24 hours, then the temporary wells on the rectangular gradient patterns, or the PDMS covering the radial patterns, were removed and each dish was cultured in low serum (0.5%) medium. Photomicrographs were taken of the leading edge at 12.5× (rectangular), or 3.5× (radial), every 24 hours for 7 days to track and measure migration.

After seven days in culture with radial gradients of immobilized EGF, HaCaTs migrated into and filled the "wound" 100%+/−0%. Controls with no patterned growth factor only filled the "wound" 32.9%+/−2.1% (p<0.001) after seven days. (FIG. 8) These radial patterns are exemplary of immobilized gradients of growth factors appropriate for the design of a dressing for a dermal wound.

At day 7 on the rectangular gradients, migration on IGF-1 [g1] and [g2] was 4 times greater than the control. Migration on EGF [g1] and [g2] was significantly greater than the control and IGF-1 [g1] and [g2], and EGF [g1] was significantly greater than [g2] by day 4. There was no significant difference between gradient patterns [g1] and [g2] in the IGF-1 samples. (FIG. 9, upper panel) These results suggest significantly greater potency of EGF vs. IGF-1 in stimulating keratinocyte migration, in addition to demonstrating the importance of gradient slope in developing optimized migration platforms. Migration on IGF-1 plus EGF [g1] is shown in FIG. 9 (lower panel) where, again, the greater comparative potency of EGF on keratinocyte migration is evident.

As can be appreciated from the foregoing examples, acceleration of wound closure via the present invention not only will result in decreased patient suffering and cost of wound treatment, but may also minimize scarring and lead to formation of a more stable closed wound. The preferred method of gradient formation allows precise control over gradient slope and density and is adaptable to form controlled, characterizable gradient patterns in both two and three dimensions. The patterned, directed cell migration system described and claimed herein allows precise control over wound repair and will have a substantial impact on the wound healing field.

Those skilled in the art will recognize, or be able to ascertain using no more than routine experimentation, numerous equivalents to the specific articles, devices, methods, assays and reagents described herein. Such equivalents are considered to be within the scope of this invention and encompassed by the following claims.

REFERENCES

1. Petrie N C, Yao F, Eriksson E. Gene therapy in wound healing. Surg Clin North Am 2003; 83: 597-616.
2. Frykberg R G, Armstrong D G, Giurini J, Edwards A, Kravette M, Kravitz S, Ross C, Stavosky J, Stuck R, Vanore J. American College of Foot and Ankle Surgeons. Diabetic foot disorders: a clinical practice guideline. American college of foot and ankle surgeons. J Foot Ankle Surg 2000; 39: S1-60.
3. Harrington C, Zagari M J, Corea J, Klitenic J. A cost analysis of diabetic lower-extremity ulcers. Diabetes Care 2000; 23:1333-8.
4. Medina A, Scott P G, Ghahary A, Tredget E E. Pathophysiology of chronic nonhealing wounds. J Burn Care Rehabil 2005; 26: 306-19.
5. National Institute of Diabetes and Digestive and Kidney Diseases (NIDDK). National diabetes statistics fact sheet. 2003.
6. Martin P. Wound healing-aiming for perfect skin regeneration. Science 1997; 276: 75-81.
7. Albrektsson T, Johansson C. Osteoinduction, osteoconduction and osseointegration. Eur Spine J 2001; 10: S96-101.

8. Ridley A J, Schwartz M A, Burridge K, Firtel R A, Ginsberg M H, Borisy G, Parsons J T, Horwitz A R. Cell migration: integrating signals from front to back. Science 2003; 302: 1704-9.
9. Iocono J A, Ehrlich H P, Gottrup F, Leaper D J. The biology of healing. In: Leaper D J, Harding K G, editors. Wounds: biology and management. New York, N.Y.: Oxford University Press, 1998: 10-22.
10. Nimni M. Polypeptide growth factors: targeted delivery systems. Biomaterials 1997; 18:1201-25.
11. Stadelmann W K, Digenis A G, Tobin G R. Physiology and healing dynamics of chronic cutaneous wounds. Am J Surg 1998; 176: 26S-38S.
12. Blakytny R, Jude E B, Martin Gibson J, Boulton A J, Ferguson M W. Lack of insulin-like growth factor 1 (IGF1) in the basal keratinocyte layer of diabetic skin and diabetic foot ulcers. J Pathol 2000; 190: 589-94.
13. Cooper D M, Yu E Z, Hennessy P, Ko F, Robson M C. Determination of endogenous cytokines in chronic wounds. Ann Surg 1994; 219: 688-92.
14. Jost M, Kari C, Rodeck U. The EGF receptor—an essential regulator of multiple epidermal functions. Eur J Dermatol 2000; 10: 505-10.
15. Grazul-Bilska A T, Johnson M L, Bilski J J, Redmer D A, Reynolds L P, Abdullah A, Abdullah K M. Wound healing: the role of growth factors. Drugs Today 2003; 39: 787-800.
16. Thomas S, Leigh I M. Wound dressings. In: Leaper D J, Harding K G, editors. Wounds: biology and management. New York, N.Y.: Oxford University Press, 1998: 166-82.
17. Bennett S P, Griffiths G D, Schor A M, Leese G P, Schor S L. Growth factors in the treatment of diabetic foot ulcers. Br J Surg 2003; 90: 133-46.
18. Wieman T J. Clinical efficacy of becaplermin (rhPDGF-BB) gel. Am J Surg 1998; 176: 74S-9S.
19. Gu D L, Nguyen T, Phillips M L, Chandler L A, Sosnowski B. Matrix-immobilized growth factor gene therapy enhances tissue repair. Wounds 2004; 16: 34-41.
20. Bennett N T, Schultz G S. Growth factors and wound healing: biochemical properties of growth factors and their receptors. Am J Surg 1993; 165: 728-37.
21. Finetti G, Farina M. Recombinant human basic-fibroblastic growth factor: different medical dressings for clinical application in wound healing. Pharmacology 1992; 47: 967-78.
22. Bhatia S N, Toner M, Tompkins R G, Yarmush M L. Selective adhesion of hepatocytes on patterned surfaces. Ann NY Acad Sci 1994; 745: 187-209.
23. Matsuda T, Inoue K, Sugawara T. Development of micropatterning technology for cultured cells. ASAIO Trans 1990; 36: M559-62.
24. Sigrist H, Gao H, Wegmuller B. Light-dependent, covalent immobilization of biomolecules on "inert" surfaces. Biotechnology (NY) 1992; 10: 1026-8.
25. Ito Y. Surface micropatterning to regulate cell function. Biomaterials 1999; 20: 2333-42.
26. Mrksich M. Tailored substrates for studies of attached cell culture. Cell Mol Life Sci 1998; 54: 653-62.
27. Ito Y, Chen G, Imanishi Y. Micropatterned immobilization of epidermal growth factor to regulate cell function. Bioconj Chem 1998; 9: 277-82.
28. Chen G, Ito Y, Imanishi Y. Photo-immobilization of epidermal growth factor enhances its mitogenic effect by artificial juxtacrine signaling. Biochim Biophys Acta 1997; 1358: 200-8.
29. Chen G, Ito Y. Gradient micropattern immobilization of EGF to investigate the effect of artificial juxtacrine stimulation. Biomaterials 2001; 22: 2453-7.
30. Vanin E F, Burkhard S J, Kaiser I I. p-azidophenylglyoxal: a heterobifunctional photosensitive reagent. FEBS Lett 1981; 124: 89-92.
31. Ngo T T, Yam C F, Lenhoff H M, Ivy J. p-azidophenylglyoxal: a heterobifunctional photoactivable cross-linking reagent selective for arginyl residues. J Biol Chem 1981; 256:11313-8.
32. Usui M L, Underwood R A, Mansbridge J N, Muffley L A, Carter W G, Olerud J E. Morphological evidence for the role of suprabasal keratinocytes in wound reepithelialization. Wound Repair Regen 2005; 13: 468-79.
33. Pozzi G, Guidi M, Laudicina F, Marazzi M, Falcone L, Betti R, Crosti C, Muller E E, DiMattia G E, Locatelli V, Torsello A. IGF-1 stimulates proliferation of spontaneously immortalized human keratinocytes (HACAT) by autocrine/paracrine mechanisms. J Endocrinol Invest 2004; 27:142-9.
34. Cass D L, Bullard K M, Sylvester K G, Yang E Y, Sheppard D, Herlyn M, Adzick N S. Epidermal integrin expression is upregulated rapidly in human fetal wound repair. J Pediatr Surg 1998; 33: 312-6.
35. Bowers K, Piper S C, Edeling M A, Gray S R, Owen D J, Lehner P J, Luzio J P. Degradation of endocytosed epidermal growth factor and virally ubiquitinated major histocompatibility complex class I is independent of mammalian ESCRTII. J Biol Chem 2006; 281: 5094-105.
36. Chan K Y, Lindquist T D, Edenfield M J, Nicolson M A, Banks A R. Pharmacokinetic study of recombinant human epidermal growth factor in the anterior eye. Invest Opthalmol V is Sci 1991; 32: 3209-15.
37. Satin B, Norais N, Telford J, Rappuoli R, Murgia M, Montecucco C, Papini E. Effect of *helicobacter pylori* vacuolating toxin on maturation and extracellular release of procathepsin D and on epidermal growth factor degradation. J Biol Chem 1997; 272: 25022-8.
38. Koivisto L, Jiang G, Hakkinen L, Chan B, Larjava H. HaCaT keratinocyte migration is dependent on epidermal growth factor receptor signaling and glycogen synthase kinase-3alpha. Exp Cell Res 2006; 312: 2791-805.
39. Bach M, Holig P, Schlosser E, Volkel T, Graser A, Muller R, Kontermann R E. Isolation from phage display libraries of lysine-deficient human epidermal growth factor variants for directional conjugation as targeting ligands. Protein Eng 2003; 16: 1107-13.
40. Hutchings H, Ortega N, Plouct J. Extracellular matrix-bound vascular endothelial growth factor promotes endothelial cell adhesion, migration, and survival through integrin ligation. FASEB J 2003; 17: 1520-2.
41. Kapur T A, Shoichet M S. Immobilized concentration gradients of nerve growth factor guide neurite outgrowth. J Biomed Mater Res A 2004; 68A: 235-43.
42. Ruehl M, Somasundaram R, Schoenfelder I, Farndale R W, Knight C G, Schmid M, Ackermann R, Riecken E O, Zeitz M, Schuppan D. The epithelial mitogen keratinocyte growth factor binds to collagens via the consensus sequence glycine-proline-hydroxyproline. J Biol Chem 2002; 277:26872-8.
43. Gobin A S, West J L. Effects of epidermal growth factor on fibroblast migration through biomimetic hydrogels. Biotechnol Prog 2003; 19: 1781-5.
44. DeLong S A, Moon J J, West J L. Covalently immobilized gradients of bFGF on hydrogel scaffolds for directed cell migration. Biomaterials 2005; 26: 3227-34.
45. Burdick J A, Khademhosseini A, Langer R. Fabrication of gradient hydrogels using a microfluidics/photopolymerization process. Langmuir 2004; 20: 5153-6.

46. Zaari N, Rajagopalan P, Kim S K, Engler A J, Wong J Y. Photopolymerization in microfluidic gradient generators: microscale control of substrate compliance to manipulate cell response. Adv Mater 2004; 16: 2133-7.
47. Luo N, Metters A T, Hutchison J B, Bowman C N, Anseth K S. A methacrylated photoiniferter as a chemical basis for microlithography: micropatterning based on photografting polymerization. Macromolecules 2003; 36: 6739-45.
48. Ando Y, Jensen P. Epidermal growth factor and insulin-like growth factor I enhance keratinocyte migration. J Invest Dermatol 1993; 100:633-39.
49. Haase I, Evans R, Pofahl R, Watt F M. Regulation of keratinocyte shape, migration and wound epithelialization by IGF-1- and EGF-dependent signalling pathways. J Cell Sci 2003; 116:3227-38.

What is claimed is:

1. A patterned gradient wound dressing for promoting directed cell migration during dermal wound healing, comprising: (a) a support substrate for placement at a dermal wound; and (b) a growth factor covalently linked to the support substrate so as to define a growth factor gradient that promotes directed cell migration from a low- to a high growth factor concentration across said growth factor gradient during dermal wound healing, said low-to-high growth factor concentrations ranging from 0 ng/cm$^2$ to about 36 ng/cm$^2$.

2. The patterned gradient wound dressing according to claim 1, wherein the growth factor gradient is characterized by an exponentially increasing concentration of growth factor.

3. The patterned gradient wound dressing according to claim 1, wherein said growth factor is selected from the group consisting of epidermal growth factor (EGF), insulin-like growth factor 1 (IGF-1), basic fibroblast growth factor (bFGF), platelet-derived growth factor (PDGF), vascular endothelial growth factor (VEGF), keratinocyte growth factor (KGF), transforming growth factor alpha (TGF-a), transforming growth factor beta (TGF-b) and mixtures thereof.

4. The patterned gradient wound dressing according to claim 1, wherein said growth factor gradient further comprises an extracellular matrix protein.

5. The patterned gradient wound dressing according to claim 1, wherein said growth factor gradient further comprises an angiogenesis factor.

6. The patterned gradient wound dressing according to claim 1, wherein said support substrate is made of a polymeric material.

7. The patterned gradient wound dressing according to claim 6, wherein said polymeric material is selected from the group consisting of polytetrafluoroethylene, polydimethylsiloxane, poly-vinylidine fluoride, polyethylene, polystyrene, polycarbonate, polyhydroxyethyl methacrylate, polyvinyl alcohol, polyvinyl chloride, polycaproamide, polyetheyleneoxide, polyethyleneterephthalate, polyacrylonitrile, silicones, polysilanes, polysiloxanes, polyurethanes, polylactides, polyglycolic acid, polybeta hydroxybutyrate, polyepisilon caprolactone, polyanhyhdrides, polyorthoesters, polyiminocarbonates, mixtures thereof and copolymers thereof.

8. The patterned gradient wound dressing according to claim 1, wherein said support substrate is made of an interpenetrating polymer network (IPN).

9. The patterned gradient wound dressing according to claim 1, wherein said support substrate is made of a sol-gel.

10. The patterned gradient wound dressing according to claim 1, wherein said support substrate is made of a hydrogel.

11. The patterned gradient wound dressing according to claim 1, wherein said support substrate is made of a natural product.

12. The patterned gradient wound dressing according to claim 11, wherein said natural product is selected from the group consisting of alginates, gelatins, collagen, fibrin, hyaluronan, cellulose, polycarbohydates, mycoses, polyxyloses, chitans, polymers of amino glucoses, tragacanths, and latexes.

13. The patterned gradient wound dressing according to claim 1, wherein said growth factor is EGF.

14. The patterned gradient wound dressing according to claim 1, wherein said growth factor gradient is spatially-oriented relative to the support substrate such that the low concentration of growth factor gradient is located along a periphery of the support substrate, wherein the low concentration of the growth factor gradient is immediately adjacent to the dermal wound when the support substrate is placed at said dermal wound.

15. The patterned gradient wound dressing according to claim 1, wherein said growth factor gradient is in the form of a two dimensional radial pattern.

16. The patterned gradient wound dressing according to claim 1, wherein said growth factor gradient is in the form of a three dimensional radial pattern.

17. The patterned gradient wound dressing according to claim 1 further comprising a photoactivatable linker that covalently links the growth factor to the support substrate, the photoactivatable linker selected from the group consisting of N-5-Azido-2-nitrobenzoyloxysuccinimide, Sulfosuccinimidyl 2-[m-azido-o-nitrobenzamido]ethyl-1,3'-dithiopropionate, N-Succinimidyl-6-[4'-azido-2'-nitrophenylamino] hexanoate, and Sulfosuccinimidyl-6-[4'-azido-2'-nitrophenylaminio]hexanoate.

18. A method for treating a dermal wound, comprising:
(a) providing a patterned gradient wound dressing including: (i) a support substrate for placement at the dermal wound; and (ii) a growth factor covalently linked to the support substrate, so as to define a growth factor gradient characterized by a concentration of growth factor that promotes directed cell migration across said growth factor gradient from low to high growth factor concentration during dermal wound healing, said low-to-high growth factor concentrations ranging from 0 ng/cm$^2$ to about 36 ng/cm$^2$; and
(b) applying said patterned gradient wound dressing to the dermal wound in the course of wound management to thereby treat said dermal wound.

19. The method according to claim 18, wherein the dermal wound is an acute dermal wound.

20. The method according to claim 18, wherein the dermal wound is a chronic dermal wound.

* * * * *